(12) United States Patent
Piazza et al.

(10) Patent No.: US 9,169,247 B2
(45) Date of Patent: Oct. 27, 2015

(54) TETRAHYDRO-BETA-CARBOLINE DERIVATIVES, SYNTHESIS AND USE THEREOF

(75) Inventors: Gary A. Piazza, Mobile, AL (US); Ashraf H. Abadi, Cairo (EG)

(73) Assignee: Southern Research Institute, Birmingham, AL (US)

( * ) Notice: Subject to any disclaimer, the term of this patent is extended or adjusted under 35 U.S.C. 154(b) by 542 days.

(21) Appl. No.: 13/510,810

(22) PCT Filed: Nov. 19, 2010

(86) PCT No.: PCT/US2010/057410
§ 371 (c)(1),
(2), (4) Date: Aug. 1, 2012

(87) PCT Pub. No.: WO2011/063223
PCT Pub. Date: May 26, 2011

(65) Prior Publication Data
US 2012/0309781 A1      Dec. 6, 2012

Related U.S. Application Data

(60) Provisional application No. 61/262,989, filed on Nov. 20, 2009.

(51) Int. Cl.
*C07D 471/04*      (2006.01)
(52) U.S. Cl.
CPC .................................. *C07D 471/04* (2013.01)

(58) Field of Classification Search
CPC ...................................................... C07D 471/04
USPC ............................................ 546/85; 514/292
See application file for complete search history.

(56) References Cited

U.S. PATENT DOCUMENTS

| | | | |
|---|---|---|---|
| 6,069,150 | A  | 5/2000 | Spinelli et al. |
| 7,223,863 | B2 | 5/2007 | Deshpande et al. |
| 2005/0096335 | A1 | 5/2005 | Mjalli et al. |

FOREIGN PATENT DOCUMENTS

| | | | |
|---|---|---|---|
| FR | 2916200 | * | 11/2008 |
| WO | WO-2005089764 A1 | | 9/2005 |
| WO | WO-2006/113703 A2 | | 10/2006 |

* cited by examiner

*Primary Examiner* — John Mabry
(74) *Attorney, Agent, or Firm* — Novak Druce Connolly Bove + Quigg LLP

(57) ABSTRACT

Certain 2-halophenyl, 2,4-dihalophenyl (e.g. 2,4-dichlorophenyl), 3,4-dichlorophenyl (e.g. 3,4-dichlorophenyl), 2,6-dichlorophenyl (2,6-dichlorophenyl) and 2,5-diakoxyphenyl (e.g. 2,5-dimethoxyphenyl) derivatives of tetrahydro-β-carbolines are provided, along with their pharmaceutically acceptable salts; prodrugs and solvates, and compositions containing the compounds. The compounds are useful for the prevention and treatment of cancer, and other indications where PDE5 inhibitors have shown benefits including erectile dysfunction, pulmonary hypertension, enhancing cognitive function, cystic fibrosis, or enhancing the activity of conventional chemotherapeutic drugs. Methods for fabricating the compounds are also provided.

14 Claims, 3 Drawing Sheets

TETRAHYDRO-BETA-CARBOLINE DERIVATIVES, SYNTHESIS AND USE THEREOF

CROSS REFERENCE TO RELATED APPLICATIONS

This application is a National Phase filing under 35 U.S.C. §371 of PCT/US2010/057410 filed on Nov. 19, 2010; and this application claims the benefit of U.S. Provisional Application No. 61/262,989 filed on Nov. 19, 2009; the entire contents of all are hereby incorporated by reference.

FEDERALLY SPONSORED RESEARCH AND DEVELOPMENT

This invention was partially supported by a grant No. 5R01CA131378 from National Institutes of Health, National Cancer Institute and the US Government has certain rights in the invention.

TECHNICAL FIELD

The present disclosure relates to derivatives of tetrahydro-β-carbolines and in particular 2-halophenyl, 2,4-dihalophenyl, 3,4-dihalophenyl, 2,6-dihalophenyl and 2,5-dialkoxyphenyl derivatives of tetrahydro-β-carbolines including 2-chlorophenyl, 2-bromophenyl, 2,4-dichlorophenyl, 3,4-dichlorophenyl, 2,6-dichlorophenyl and 2,5-dimethoxyphenyl derivatives of tetrahydro-β-carbolines. The present disclosure also relates to pharmaceutical compositions comprising the disclosed derivatives of tetrahydro-β-carbolines, as well as a method of using the compounds for the prevention or treatment of cancer in a mammal. In addition, the disclosed compounds are for other indications where PDE5 inhibitors have shown benefits including erectile dysfunction, pulmonary hypertension, enhancing cognitive function, cystic fibrosis, or enhancing the activity of conventional chemotherapeutic drugs. The present disclosure also relates to a method for producing the disclosed compounds.

BACKGROUND OF DISCLOSURE

Phosphodiesterase type 5 (PDE5) is an important enzyme involved in regulating intracellular cyclic guanosine monophosphate (cGMP) signaling. PDE5 catalyzes the hydrolysis of cGMP into 5' guanosine monophosphate, whereby inhibition leads to increased magnitude or duration of the cGMP signal. PDE5 is an essential regulator of normal physiological processes, such as smooth muscle contraction and relaxation and may also play an important role in a variety of pathological conditions including pulmonary hypertension, cognitive function, cystic fibrosis, and cancer. For example, PDE5 is a major cGMP degrading PDE isozyme in penile corpus cavernosum tissue, whereby its inhibition by drugs such as sildenafil, vardenafil, or tadalafil can enhance penile erection upon sexual arousal.[1,2] Inhibition of PDE5 may also benefit patients with pulmonary hypertension or cystic fibrosis, while additional indications are being studied including the enhancement of cognitive function, increasing efficacy of conventional chemotherapy, as well as being cardioprotective.

Recent studies have shown that PDE5 and possibly additional cGMP-PDEs are expressed in various carcinomas such as those derived from the colon, breast, lung and bladder. Moreover, cGMP PDE inhibition and consequent high intracellular levels of cGMP may be associated with the apoptotic activities of certain drugs.[4,5] For example, exisulind and its analogs (CP78, CP461, CP248) have been reported to selectively induce apoptosis of tumor cells derived from a variety of cancers including colon, bladder, prostate, breast and lung. Exisulind and its analogs maintained similar rank order of potency to induce apoptosis and inhibit tumor cell growth compared with cGMP PDE inhibition. Such compounds also caused a sustained elevation of intracellular cGMP levels in colon tumor cells. Therefore, it is proposed that cGMP mediates the mechanism underlying the apoptosis inducing properties of exisulind in neoplastic cells.[4-7] These effects in neoplastic cells appear to be not solely dependent on the specific inhibition of PDE5, but rather, are related to inhibition of additional cGMP-PDEs. Previous studies therefore indicate that it is important to inhibit multiple cGMP PDE isoforms, although the exact isozymes involved have not been well defined.[7] Accordingly, highly selective and potent PDE5 inhibitors such as tadalafil would not be expected to have anticancer properties. Additionally, there may be other reasons why conventional PDE5 inhibitors do not have anticancer activity that have not yet been delineated.

Even though significant advances have occurred in the treatment of cancer, it still remains a major worldwide health concern. Notwithstanding the advances in treatments for cancer and other hyperproliferative diseases there still remains room for improved drugs that are effective with minimal toxicity.

SUMMARY OF DISCLOSURE

The present disclosure relates to compounds represented by the following formulae (1) and (2):

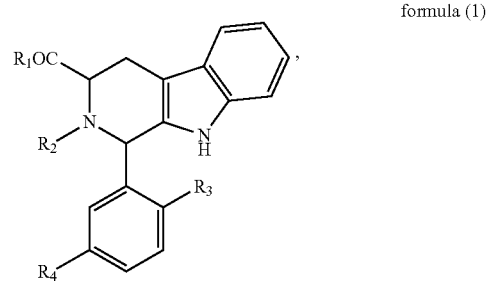

formula (1)

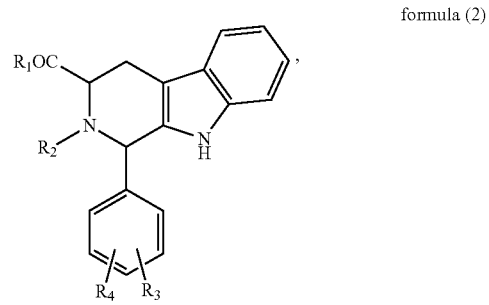

formula (2)

wherein in formula (1), $R_1$ is a hydroxy or an alkoxy group containing 1-4 carbon atoms; $R_2$ is an acyl halo group containing 2-3 carbon atoms; $R_3$ is a halo group or an alkoxy group containing 1-4 carbon atoms and $R_4$ is H when $R_3$ is halo and is an alkoxy group containing 1-4 carbon atoms when $R_3$ is an alkoxy group containing 1-4 carbon atoms; pharmaceutically acceptable salt thereof; prodrugs thereof or solvates thereof; and wherein in formula (2), $R_1$ is a hydroxy or an alkoxy group containing 1-4 carbon atoms; $R_2$ is an acyl halo group containing 2-3 carbon atoms; $R_3$ is a halo group and $R_4$ is H or halo; pharmaceutically acceptable salt thereof; prodrugs thereof or solvates thereof.

Another aspect of the present disclosure relates to pharmaceutical compositions containing a compound represented by formula (1) and/or formula (2); pharmaceutically acceptable salt thereof; prodrug thereof or solvate thereof.

A still further aspect of the present invention relates to a method for preventing or treating a mammalian host at risk of developing cancer or has been diagnosed with cancer, which comprises administering to said host an effective amount of at least one compound represented by the formula (1) or formula (2) or both; a pharmaceutically acceptable salt thereof; a prodrug thereof or a solvate thereof; alone or in combination with known preventive or therapeutic drugs.

Another aspect of the present disclosure relates to treating men with erectile dysfunction by administering an amount effective for treating erectile dysfunction of at least one compound represented by the formula (1) or formula (2) or both; a pharmaceutically acceptable salt thereof; a prodrug thereof or a solvate thereof; alone or in combination with known drugs that are useful for treating erectile dysfunction.

A still further aspect of the present disclosure relates to treating a mammalian host suffering from pulmonary hypertension, which comprises administering to the host an amount effective for treating pulmonary hypertension of at least one compound represented by the formula (1) or formula (2) or both; a pharmaceutically acceptable salt thereof; a prodrug thereof or a solvate thereof; alone or in combination with known drugs that are useful for pulmonary hypertension.

The present disclosure also relates to methods for preparing compounds according to formulae (1) and (2) above.

Still other objects and advantages of the present disclosure will become readily apparent by those skilled in the art from the following detailed description, wherein it is shown and described only the preferred embodiments, simply by way of illustration of the best mode. As will be realized, the disclosure is capable of other and different embodiments, and its several details are capable of modifications in various obvious respects, without departing from the disclosure. Accordingly, the description is to be regarded as illustrative in nature and not as restrictive.

BRIEF DESCRIPTION OF DRAWINGS

FIG. 1A illustrates the induction of intracellular cGMP levels in cultured human MDA-MB-231 breast tumor cells treated for 30 minutes with compound 2f. FIG. 1B illustrates the inability of tadalafil to alter cGMP levels in human MDA-MB-231 breast tumor cells. The + indicates the effects of a positive control, sulindac sulfide tested at 100 μM. The cells were treated for 30 minutes prior to measuring intracellular cGMP levels by immunoassay. The * indicates statistical significance with $p<0.05$.

FIG. 3A shows in vitro tumor cell growth inhibitory activity of compound 2j in the human Caki-1 renal tumor cell line with an $IC_{50}$ value of 2.3 nM. The cells with treated for 72 hours prior to measuring cell viability using the Cell Titer Glo assay (Promega Corp.). FIG. 3B shows in vivo tumor growth inhibitory of compound 2j using the human Caki-1 renal tumor mouse xenograft model. Tumor bearing mice were treated at a dose of 10 mg/kg one time per day for 22 days.

BEST AND VARIOUS MODES

Figure 1:
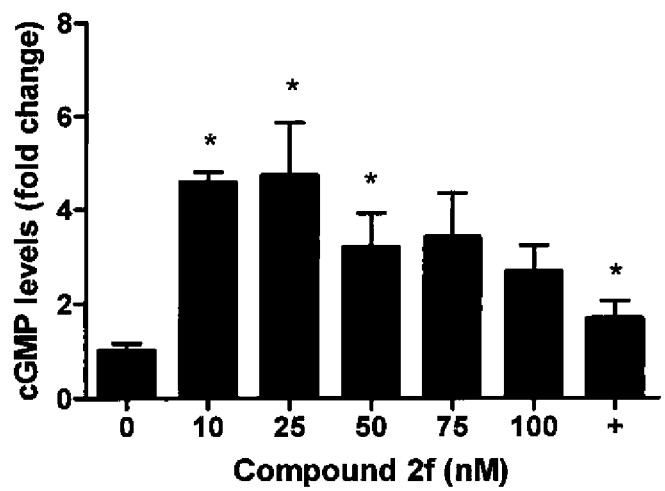
FIGS. 1A-B illustrate the effect of compound 2f and tadalafil on cGMP elevation in human MDA-MB-231 breast tumor cells.
Figure 1B:
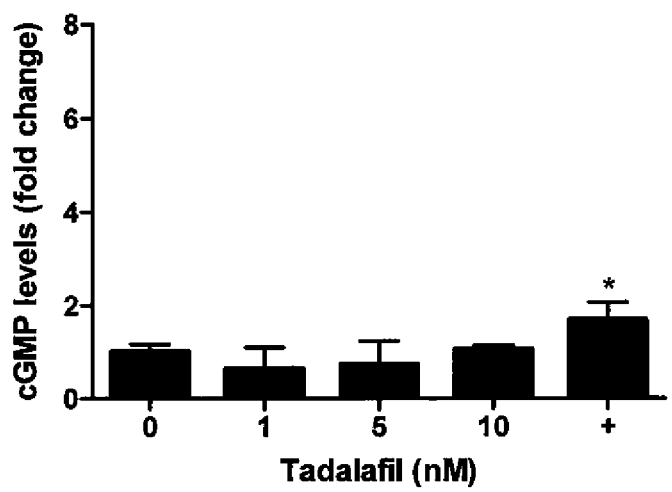

The present disclosure relates to compounds represented by the following formulae (1) and (2):

formula (1)

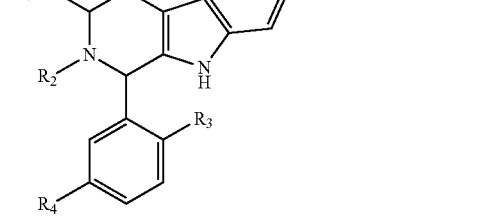

formula (2)

wherein in formula (1), $R_1$ is a hydroxy or an alkoxy group containing 1-4 carbon atoms; $R_2$ is an acyl halo group containing 2-3 carbon atoms; $R_3$ is a halo group or an alkoxy group containing 1-4 carbon atoms and $R_4$ is H when $R_3$ is halo and is an alkoxy group containing 1-4 carbon atoms when $R_3$ is an alkoxy group containing 1-4 carbon atoms; pharmaceutically acceptable salt thereof; prodrugs thereof or solvates thereof; and wherein in formula (2), $R_1$ is a hydroxy or an alkoxy group containing 1-4 carbon atoms; $R_2$ is an acyl halo group containing 2-3 carbon atoms; $R_3$ is a halo group and $R_4$ is H or halo; pharmaceutically acceptable salt thereof; prodrugs thereof or solvates thereof.

It is noted that in the interest of avoiding overlap between formula (1) and formula (2), that when $R_3$ is in position 2 and $R_4$ is in position 5, $R_4$ is halo and not H.

Examples of alkoxy groups include methoxy, ethoxy, propoxy and butoxy, with methoxy being most typical.

Examples of halo groups include chloro, bromo and fluoro. The most typical halo group employed in the $R_2$ acylhalo group is chloro, and the most typical halo group for $R_3$ is chloro or bromo and the most typical groups for $R_4$ are hydrogen, methoxy or chloro. The most typical acylhalo group for $R_2$ is ethanoyl chloride.

It is of course understood that the compounds of the present disclosure relate to all optical isomers and stereo-isomers at the various possible atoms of the molecule, unless specified otherwise.

A "prodrug" is a compound that is converted within the body into its active form that has a medical effect. Prodrugs may be useful when the active drug may be too toxic to administer systemically, the active drug is absorbed poorly by the digestive tract, or the body breaks down the active drug before it reaches its target. Methods of making prodrugs are disclosed in Hans Bundgaard, DESIGN OF PRODRUGS (Elsevier Science Publishers B.V. 1985), which is incorporated herein by reference in its entirety.

Prodrug forms of the compounds bearing various nitrogen functions (amino, hydroxyamino, hydrazino, guanidino, amidino, amide, etc.) may include the following types of derivatives where each R group individually may be hydrogen, substituted or unsubstituted alkyl, aryl, alkenyl, alkynyl, heterocycle, alkylaryl, aralkyl, aralkenyl, aralkynyl, cycloalkyl or cycloalkenyl groups as defined above.

Carboxamides, —NHC(O)R
Carbamates, —NHC(O)OR
(Acyloxy)alkyl Carbamates, NHC(O)OROC(O)R
Enamines, —NHCR(=CHCRO$_2$R) or —NHCR(=CHCRONR$_2$)
Schiff Bases, —N=CR$_2$
Mannich Bases (from carboximide compounds), RCONHCH$_2$NR$_2$ Preparations of such prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compound of the invention.

Prodrug forms of carboxyl-bearing compounds of the disclosure include esters (—CO$_2$R) where the R group corresponds to any alcohol whose release in the body through enzymatic or hydrolytic processes would be at pharmaceutically acceptable levels. Another prodrug derived from a carboxylic acid form of the disclosure may be a quaternary salt type of structure described by Bodor et al., J. Med. Chem. 1980, 23, 469.

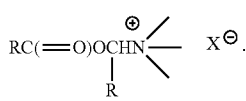

III

"Pharmaceutically acceptable salts" refer to derivatives of the disclosed compounds wherein the parent compound is modified by making acid or base salts thereof. The compounds of this disclosure form acid and base addition salts with a wide variety of organic and inorganic acids and bases and includes the physiologically acceptable salts which are often used in pharmaceutical chemistry. Such salts are also part of this disclosure. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkonic acids, hydroxyalkanoic and hydroxyalkandioic acids, aromatic acids, aliphatic and aromatic sulfonic acids may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, cabrate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromobenzenesulfonate, chlorobenzenesulfonate, ethanesulfonate, 2-hydroxyethanesulfonate, methanesulfonate, naphthalene-1-sulfonate, naphthalene-2-sulfonate, p-toleunesulfonate, xylenesulfonate, tartarate, and the like.

Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include sodium hydroxide, potassium hydroxide, ammonium hydroxide, potassium carbonate, methylamine, diethylamine, and ethylene diamine.

"Solvates" refers to the compound formed by the interaction of a solvent and a solute and includes hydrates. Solvates are usually crystalline solid adducts containing solvent molecules within the crystal structure, in either stoichiometric or nonstoichiometric proportions.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

The general synthesis of the target derivatives is illustrated in the reaction schemes below:

Scheme 1:

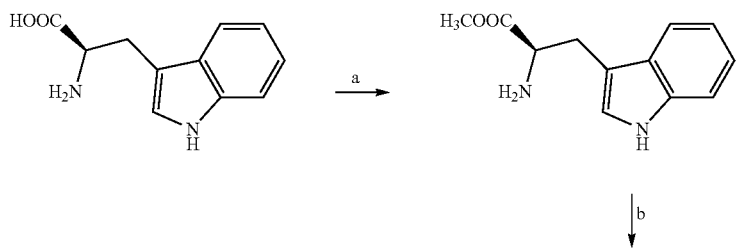

7 8

-continued

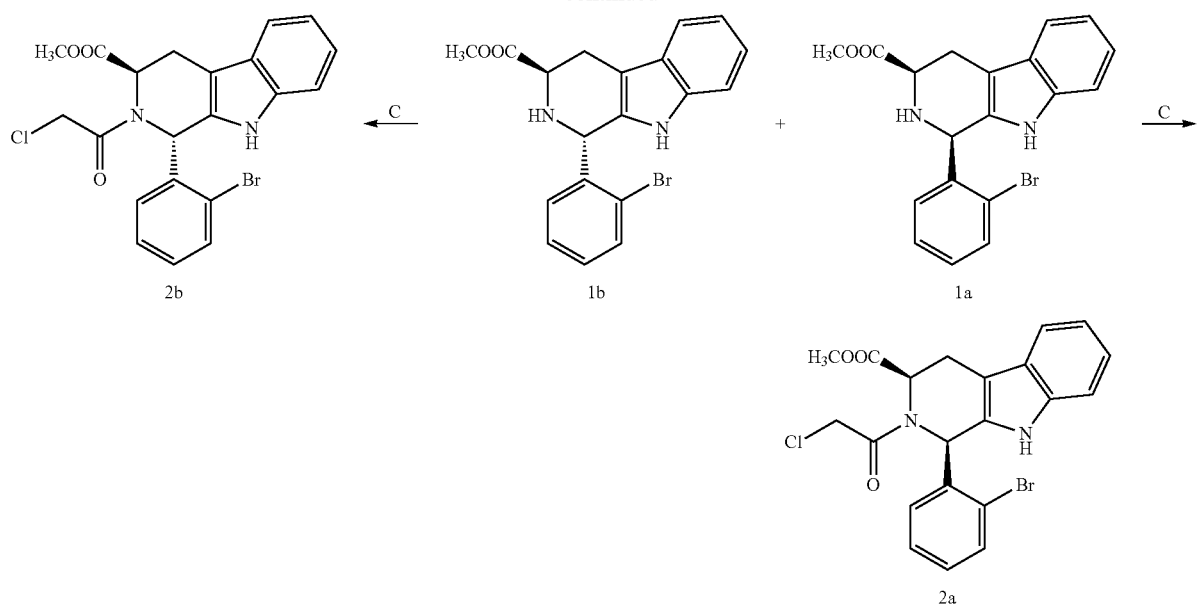

The 2 diastereomers were separated by column chromatography

Conditions: (a): CH₃OH/CH₃COCl/reflux for 5 hrs/neutralization; (b): 2-bromobenzaldehyde/CF₃COOH/room temperature; (c): ClCH₂COCl/NaHCO₃/CHCl₃

Scheme 2:

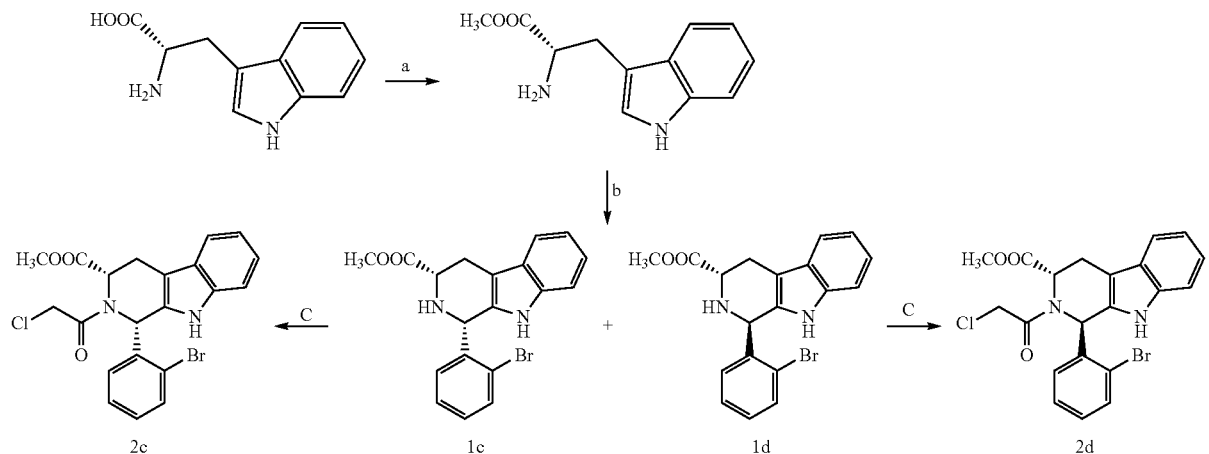

The 2 diastereomers were separated by column chromatography

Conditions: (a): CH₃OH/CH₃COCl/reflux for 5 hrs/neutralization; (b): 2-bromobenzaldehyde/CF₃COOH/room temperature; (c): ClCH₂COCl/NaHCO₃/CHCl₃

Scheme 3:

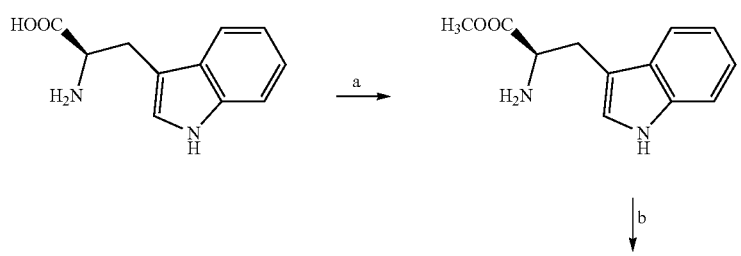

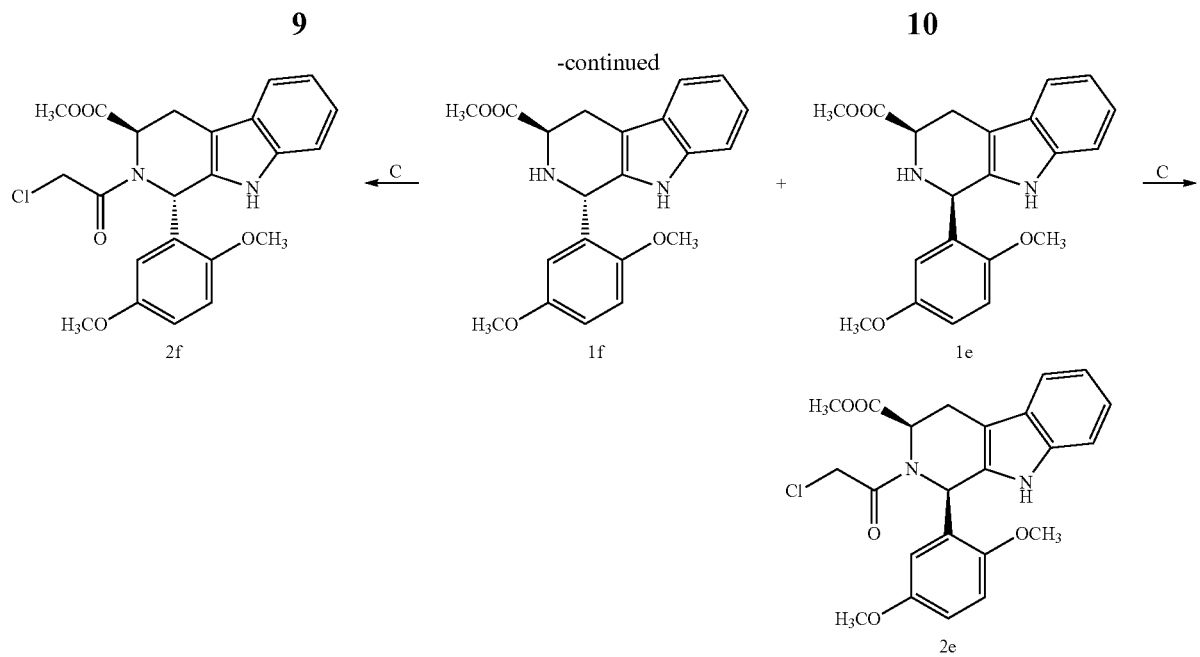

The 2 diastereomers were separated by column chromatography

Conditions: (a): CH₃OH/CH₃COCl/reflux for 5 hrs/neutralization; (b): 2,5-dimethoxybenzaldehyde/CF₃COOH/room temperature; (c): ClCH₂COCl/NaHCO₃/CHCl₃

Scheme 4:

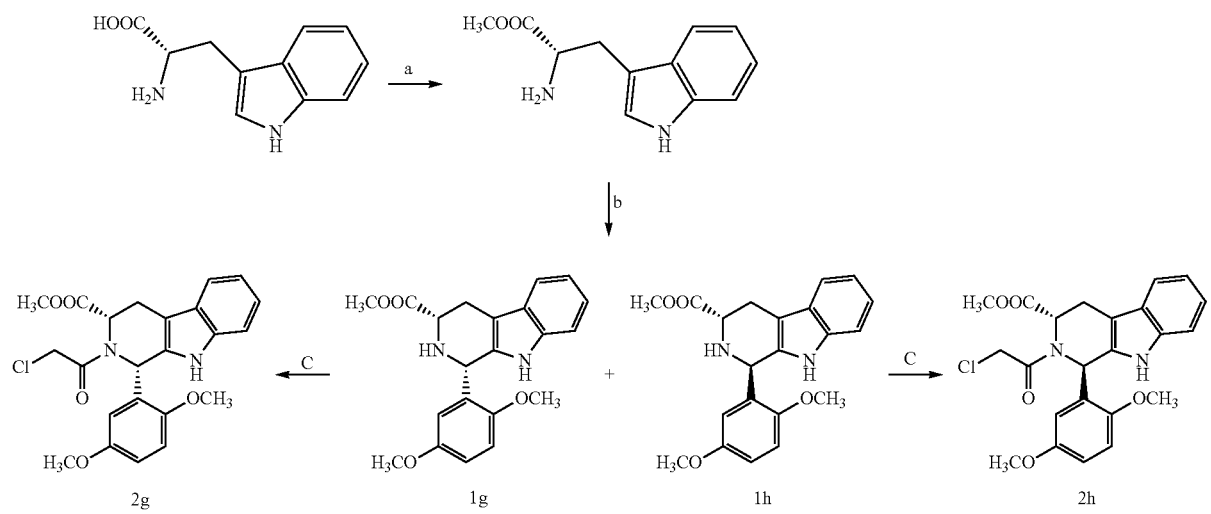

The 2 diastereomers were separated by column chromatography

Conditions: (a): CH₃OH/CH₃COCl/reflux for 5 hrs/neutralization; (b): 2,5-dimethoxybenzaldehyde/CF₃COOH/room temperature; (c): ClCH₂COCl/NaHCO₃/CHCl₃

Scheme 5:

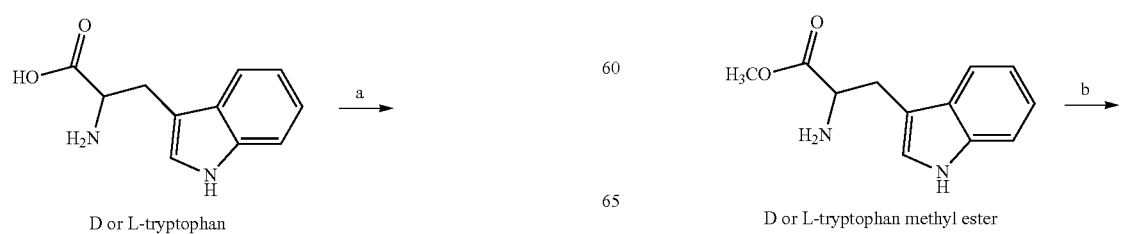

D or L-tryptophan

D or L-tryptophan methyl ester

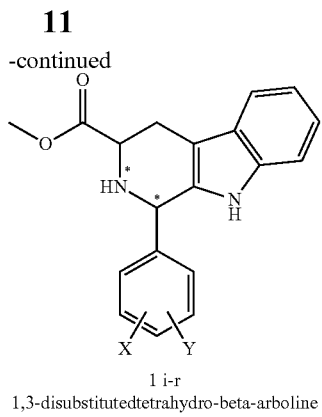

1 i-r
1,3-disubstitutedtetrahydro-beta-arboline

↓

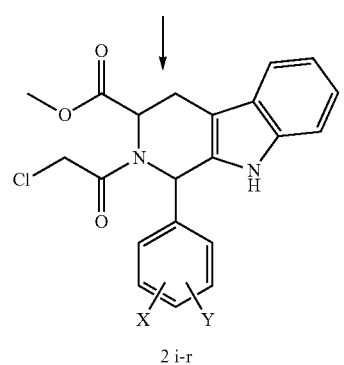

2 i-r conditions: (a) CH₃COCl/methanol/reflux/6 hrs, basify and extract with CH₂Cl₂; (b) 2,4-dichlorobenzaldehyde, 3,4-dichlorobenzaldehyde or 2,6-dichlorobenzaldehyde/TFA/4 days/RT; (c): ClCH₂COCl/NaHCO₃/CHCl₃. For exact individual assignment, see Table 1.

Both D-tryptophan and L-tryptophan methyl ester were synthesized by a general synthetic procedure for amino acid esters.[8] The D- and L-Tryptophan methyl esters and 2-bromobenzaldehyde, 2,5-dimethoxybenzaldehyde, 2,4-dichlorobenzaldehyde, 3,4-dichlorobenzaldehyde or 2,6-dichlorobenzaldehdye were subjected to Pictet-Spengler reaction under non-stereospecific conditions to give the corresponding cis- and trans-1,3-disubstituted THBCs (1a-r). It is worthy to mention that 2,6-dichlorobenzaldehdye gave only the cis isomer. See the examples presented herein below. The produced cis- and trans-diastereomers of the 1,3-disubistituted THBC, if any were separated by column chromatography using $CH_2Cl_2$ as an eluent. Reaction of the respective THBC with chloroacetyl chloride provided the corresponding amide derivative (2a-r). See the examples presented herein below.

The cis/trans stereochemistry for the THBCs (1a-r) was assigned depending on the comprehensive study of $^{13}C$ NMR spectroscopy data established in previous literature, the signals for C-1 in the trans diastereomers were clearly at a lower δ or ppm value in the $^{13}C$ NMR from those of the corresponding cis isomers in the carbon spectrum. This is probably due to the 1,3 interactions present in the trans-isomer.[9-11]

Moreover, a correlation exists between $R_f$ value on TLC and the stereochemistry of the 1,3-disubstituted THBC 1a-r, where cis-isomer is systematically less polar than the trans isomer, if any[12].

Mass spectrometry to derivatives 1a-d and 2a-d showed the molecular ion peaks at m/z $M^+$ and $M^+ +2$ due to the isotopic nature of bromine atom. Derivatives 1i-r and 2a-r showed molecular ion peaks at $M^+$ and $M^+ +2$ and $M^+ +4$ in the ratio of 9:6:1, a pattern characteristic of dichloro compounds. Moreover, the 1,3-disubstituted THBC derivatives 1a-r showed molecular ion peaks that were also the base peaks indicating their stable nature.

$^1$H-NMR of the amides 2a-r showed a peak at about 4.2 ppm due to the protons of the —$CH_2Cl$ function.

RESULTS AND DISCUSSION

Most of compounds were evaluated for in vitro tumor cell growth inhibitory activity in 2 steps; first, the percentage inhibition at a concentration of 100 μM was performed in triplicate, then for compounds displaying a percentage of inhibition >70% were evaluated by testing a range of 10 concentrations with at least two replicates per concentration to calculate an $IC_{50}$ value. The results are summarized in Table 1 and 2.

TABLE 1

Tumor cell growth inhibitory activity of 1,3-disubstituted-tetrahydro-β-carbolines against human MDA-MB-231 breast tumor cells.

| Cpd # | Stereochemistry | X, Y | % Growth Inhibition at 10 μM | Growth Inhibition $IC_{50}$, μM (95% CI) |
|---|---|---|---|---|
| 1i | 1R, 3R | 2,4-dichloro | 29 +/− 2.16 | ND |
| 1j | 1S, 3R | 2,4-dichloro | 78 +/− 1.02 | 6.73 (2.21-20.5) |
| 1k | 1S, 3S | 2,4-dichloro | 50 +/− 1.05 | ND |
| 1l | 1R, 3S | 2,4-dichloro | 28 +/− 0.13 | ND |
| 1m | 1R, 3R | 3,4-dichloro | 43 +/− 2.41 | ND |
| 1n | 1S, 3R | 3,4-dichloro | 100 +/− 0.02 | 4.62 (4.09-5.23) |
| 1o | 1S, 3S | 3,4-dichloro | 62 +/− 0.49 | 6.98 (5.93-8.22) |
| 1p | 1R, 3S | 3,4-dichloro | 48 +/− 2.12 | ND |
| 1q | 1R, 3R | 2,6-dichloro | 25 +/− 0.07 | ND |
| 1r | 1S, 3S | 2,6-dichloro | 52 +/− 0.40 | ND |

TABLE 2

Tumor cell growth inhibitory activity of 1,2,3-trisubstituted-tetrahydro-β-carbolines against human MDA-MB-231 breast tumor cells.

| Cpd # | Stereochemistry | X, Y | % Growth Inhibition at 10 μM | Growth Inhibition $IC_{50}$, μM (95% CI) |
|---|---|---|---|---|
| 2i | 1R, 3R | 2,4-dichloro | 98 +/− 0.01 | 0.56 (0.52-0.61) |
| 2j | 1S, 3R | 2,4-dichloro | 98 +/− 0.07 | 0.07 (0.05-0.11) |
| 2k | 1S, 3S | 2,4-dichloro | 55 +/− 0.039 | ND |
| 2l | 1R, 3S | 2,4-dichloro | 98 +/− 0.003 | 1.24 (1.05-1.48) |
| 2m | 1R, 3R | 3,4-dichloro | 40 +/− 2.46 | ND |
| 2n | 1S, 3R | 3,4-dichloro | 50 +/− 0.10 | ND |
| 2o | 1S, 3S | 3,4-dichloro | 43 +/− 4.95 | ND |
| 2p | 1R, 3S | 3,4-dichloro | 55 +/− 1.07 | ND |
| 2q | 1R, 3R | 2,6-dichloro | 99 +/− 0.01 | 0.05 (0.04-0.05) |
| 2r | 1S, 3S | 2,6-dichloro | 24 +/− 0.54 | 0.42 (0.35-0.51) |

Compounds 2a-h were tested for tumor cell growth inhibitory activity using the human breast MDA-MB-231 and ZR75-1 tumor cell lines and the colon CACO-2, SW-1116, and HT-29 tumor cell lines. The results are summarized in Table 3.

TABLE 3

Inhibitory effect (IC$_{50}$ value, μM) of example compounds on the growth of human breast and colon tumor cell lines. ND = Not determined.

| Cmpd# | Chemical structure | Stereo-chemistry | MDA-MB-231 | ZR75-1 | CACO-2 | SW1116 | HT-29 |
|---|---|---|---|---|---|---|---|
| 2a | 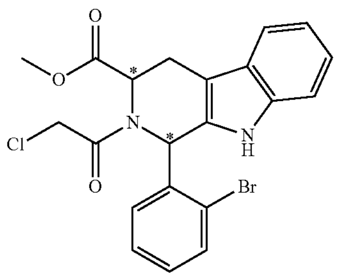 [SMILES: COC(=O)C1Cc2c([nH]c3ccccc23)C(c2ccccc2Br)N1C(=O)CCl] | 1R,3R | 0.06 | 3.52 | 0.79 | 2.79 | 1.90 |
| 2b | | 1S,3R | 0.02 | 1.10 | 1.60 | 4.30 | 1.16 |
| 2c | | 1S,3S | 0.02 | 1.10 | 0.10 | 2.72 | 0.77 |
| 2d | | 1R,3S | 0.25 | 3.61 | 0.55 | 1.05 | 3.20 |
| 2e | 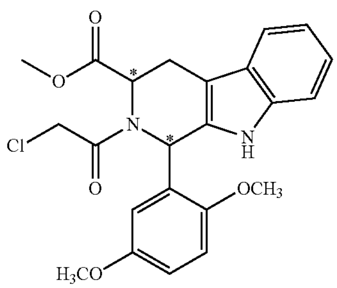 [SMILES: COC(=O)C1Cc2c([nH]c3ccccc23)C(c2cc(OC)ccc2OC)N1C(=O)CCl] | 1R,3R | 4.25 | 5.70 | 3.50 | 7.20 | 3.38 |
| 2f | | 1S,3R | 0.006 | 1.20 | 0.01 | 4.40 | 0.45 |
| 2g | | 1S,3S | 1.60 | 4.13 | 3.04 | 3.71 | 6.12 |
| 2h | | 1R,3S | 0.04 | 3.95 | 0.29 | >10 | 5.59 |
| 2i | 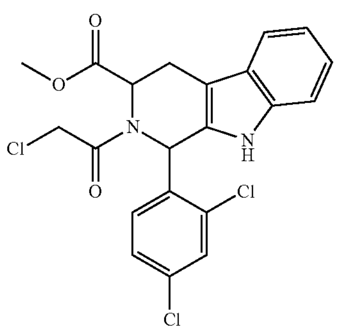 [SMILES: COC(=O)C1Cc2c([nH]c3ccccc23)C(c2ccc(Cl)cc2Cl)N1C(=O)CCl] | 1R,3R | 0.56 | ND | ND | ND | ND |
| 2j | | 1S,3R | 0.07 | ND | ND | ND | ND |
| 2k | | 1S,3S | 0.38 | ND | ND | ND | ND |
| 2l | | 1R,3S | 1.24 | ND | ND | ND | ND |
| 2m | 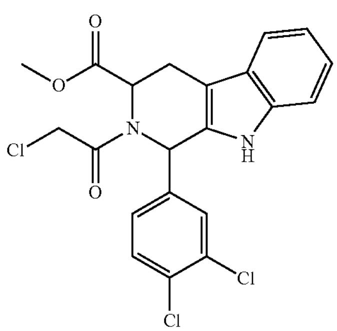 [SMILES: COC(=O)C1Cc2c([nH]c3ccccc23)C(c2ccc(Cl)c(Cl)c2)N1C(=O)CCl] | 1R,3R | >10 | ND | ND | ND | ND |
| 2n | | 1S,3R | 1.2 | ND | ND | ND | >10 |
| 2o | | 1S,3S | >10 | ND | ND | ND | ND |
| 2p | | 1R,3S | >10 | ND | ND | ND | >10 |
| 2q | 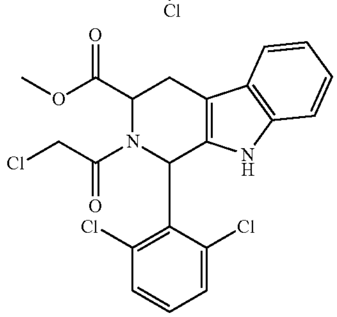 | 1R,3R | 0.04 | ND | ND | ND | 1.5 |
| 2r | | 1S,3S | 0.44 | ND | ND | ND | 1.0 |

From Table 3, compounds (2a-f, 2i, 2j, 2k, 2l, 2n, 2q and 2r) showed appreciable activity to inhibit the growth of human breast and colon tumor cell lines with $IC_{50}$ ranging from 0.006-7.20 μM. Compound 2f was the most active in the MDA-MB-231 with an $IC_{50}$ value of 0.006 μM. Compound 2f was also tested in a large panel of human tumor cell lines derived from histologically diverse tumor types. As shown in Table 4 and as evident by low $IC_{50}$ values, compound 2f displayed potent broad spectrum growth inhibitory activity against the majority of the tumor types that were tested, but was especially active against tumor cells derived from hematological and renal tumors, as well as estrogen-receptor, progesterone receptor, and Her2 negative (triple negative) breast tumor cell lines. The high potency was especially noteworthy in the NCI/ADR-RES tumor cell line, which is known to over express the drug efflux protein, P-glycoprotein (ABCB1) that mediates resistance to multiple chemotherapeutic drugs. By contrast, normal human mammary epithelial cells (HMEC) was found to be insensitive to compound 2f, which reflects as an element of tumor selectivity and a potential safety advantage of the compound compared with conventional chemotherapeutic drugs.

Figure 2:
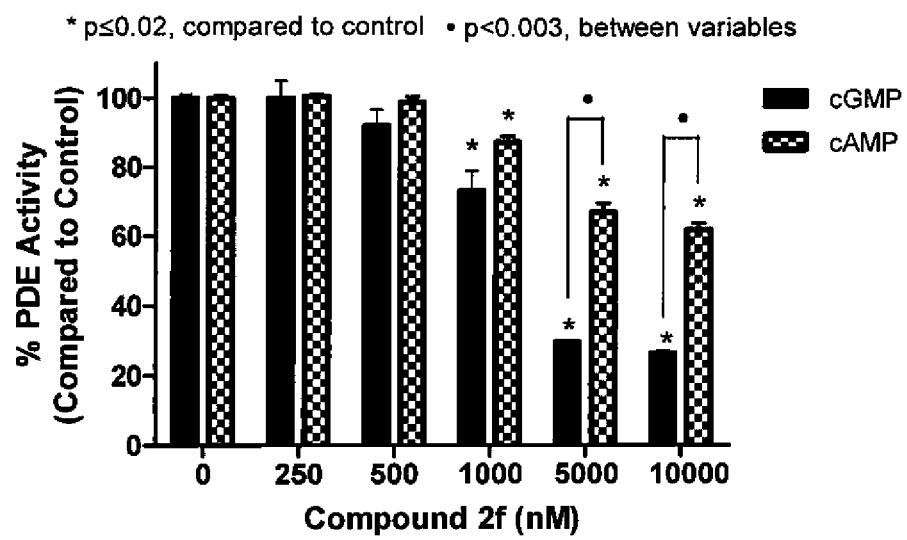
FIG. 2 illustrates cGMP phosphodiesterase inhibitory activity of compound 2f. Whole cell lysates from human MDA-MB-231 breast tumor cells treated for 18 hours with compound 2f were assayed for cGMP phosphodiesterase activity using a fluorescence polarization assay (Molecular Devices Inc).

The mechanism of action by which these compounds inhibit tumor cell growth is believed to involve the inhibition of cGMP PDE isozymes that are expressed in sensitive tumor cells. As evidence for this mechanism, the ability of compound 2f to increase intracellular cGMP levels in human MDA-MB-231 breast tumor (triple negative) cells at concentrations that inhibit tumor growth is shown in FIG. 1. The uniqueness of this compound compared with tadalafil, which does not inhibit tumor cell growth, is evident by its ability to increase cyclic GMP levels in MDA-MB-231 tumor cells, whereas tadalafil was ineffective. Consistent with these observations, compound 2f selectively inhibited cGMP PDE activity in lysates from MDA-MB-231 breast tumor cells as shown in FIG. 2.

Figure 3A:
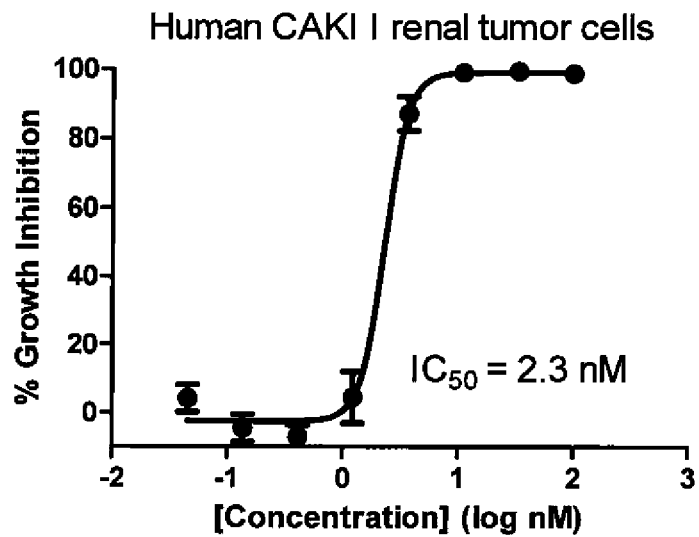
FIGS. 3A-B illustrate the anticancer activity of compound 2j.
Figure 3B:
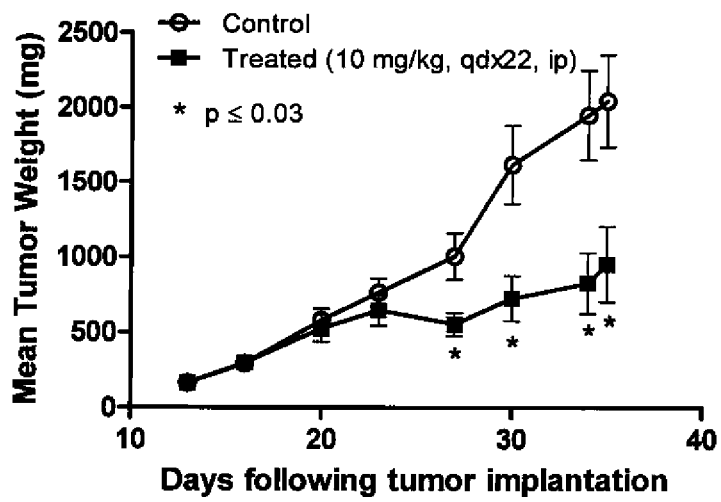

Compound 2j was also found to be highly potent by testing in a large panel of human tumor cell lines as summarized in Table 5. As shown in FIG. 3, compound 2j inhibited the growth of human Caki-1 renal tumor cells with an $IC_{50}$ value of 0.002 μM. To demonstrate the in vivo antitumor efficacy of this class of compounds, compound 2j was evaluated in the human Caki-1 renal tumor mouse xenograft model. As shown in FIG. 3, compound 2j strongly suppressed tumor growth in this experimental mouse model.

TABLE 4

Growth inhibitory activity of compound 2f in a panel of human tumor cell lines.

| Origin | Cell Line | Compound 2f $IC_{50}$ (μM) | Origin | Cell Line | Compound 2f $IC_{50}$ (μM) |
|---|---|---|---|---|---|
| Hematopoietic | CCFR-CEM | <0.006 | Breast | T-47D | 0.973 |
| | SR | <0.007 | | MDA-MB-231 | 0.006 |
| | HL-60(TB) | 0.017 | | MCF-7 | 3.75 |
| | RPMI-8226 | 0.017 | Ovarian | OVCAR-5 | 1.004 |
| | MOLT-4 | 0.161 | | OVCAR-8 | 0.068 |
| Colon | HCT-15 | >10 | | OVCAR-4 | 0.015 |
| | HCT-116 | >10 | | IGROVI | 0.01 |
| | KM12 | 1.37 | | SKOV-3 | 0.060 |
| | SW-620 | 3.31 | Prostate | DU-145 | 0.232 |
| | HT29 | 0.452 | | PC-3 | 0.192 |
| Lung | NCI-H460 | >10 | Melanoma | UACC-62 | 0.119 |
| | NCI-H322M | 2.46 | | UACC-257 | 5.32 |
| | NCI-H23 | 0.013 | | LOX IMVI | 0.004 |
| | EKVX | 0.014 | | M14 | 0.485 |
| | HOP-62 | 0.020 | | MALME-3M | 0.132 |
| Renal | ACHN | .0013 | CNS | SK-MEL-28 | 0.485 |
| | UO-31 | <0.009 | | SNB-75 | 0.063 |
| | CAKI-1 | <0.006 | | U251 | 0.259 |
| | RXF-393 | 0.003 | | SF-268 | 0.69 |
| | SN12C | 0.375 | | SNB-19 | 0.131 |
| | 786-0 | 0.032 | | SF-539 | 0.034 |
| | TK-10 | 0.078 | Multi-drug resistant | NCI-ADR-RES | 0.023 |

TABLE 5

Growth inhibitory activity of compound 2j in a panel of human tumor cell lines.

| Origin | Cell Line | Compound 2j $IC_{50}$ (μM) | Origin | Cell Line | Compound 2j $IC_{50}$ (μM) |
|---|---|---|---|---|---|
| Hematopoietic | CCFR-CEM | 0.01 | Breast | T-47D | 0.12 |
| | SR | .008 | | MDA-MB-231 | 0.03 |
| | HL-60(TB) | 0.04 | | MDA-MB-468 | 0.13 |
| | K562 | 1.25 | | BT-549 | 0.76 |
| | RPMI-8226 | 0.08 | | Hs578T | 0.22 |
| | MOLT-4 | 0.13 | | MCF-7 | >3.0 |
| Colon | HCT-15 | >3.0 | Ovarian | OVCAR-5 | 0.49 |
| | HCT-116 | >3.0 | | OVCAR-8 | 0.05 |
| | HCC-2998 | 2.26 | | OVCAR-4 | 0.05 |
| | KM12 | 0.63 | | OVCAR-3 | 0.13 |
| | SW-620 | 2.75 | | IGROV-1 | 0.02 |
| | COLO205 | 1.44 | | SK-OV-3 | 0.32 |
| | HT29 | 0.65 | Prostate | DU-145 | >3.0 |

TABLE 5-continued

Growth inhibitory activity of compound 2j in a panel of human tumor cell lines.

| Origin | Cell Line | Compound 2j IC$_{50}$ (µM) | Origin | Cell Line | Compound 2j IC$_{50}$ (µM) |
|---|---|---|---|---|---|
| Lung | NCI-H522 | 0.016 | | PC-3 | 0.34 |
| | NCI-H460 | <0.001 | Melanoma | UACC-62 | 0.29 |
| | NCI-H322M | >3.0 | | UACC-257 | >3.0 |
| | NCI-H23 | >3.0 | | LOX IMV1 | <0.001 |
| | NCI-H226 | 1.41 | | M14 | 2.26 |
| | A549 | >3.0 | | MALME-3M | >3.0 |
| | EKVX | 0.02 | | MDA-MB-435 | 0.64 |
| | HOP-62 | 0.20 | | SK-MEL-2 | 0.92 |
| | HOP-92 | 0.02 | | SK-MEL-5 | >3.0 |
| Renal | ACHN | 0.01 | | SK-MEL-28 | 1.04 |
| | UO-31 | 0.005 | CNS | SNB-75 | 0.10 |
| | CAKI-1 | 0.007 | | U251 | 1.88 |
| | A498 | 0.096 | | SF-268 | 0.10 |
| | RXF-393 | 0.015 | | SNB-19 | 1.04 |
| | SN12C | >3.0 | | SF-539 | 0.16 |
| | 786-0 | 0.02 | | SF-295 | 0.07 |
| | TK-10 | 0.20 | Multi-drug resistant | NCI-ADR/RES | 0.02 |

CONCLUSIONS

Novel derivatives of the general formulae (1) and (2)-[(2-halophenyl), 2,4-dichlorophenyl, 3,4-dichlorophenyl, 2,6-duchlorophenyl or 2,5-dimethoxyphenyl]-2-haloalkanone-3-alkyl carboxylate and their carboxylic acid derivatives were synthesized. Their chemical structures were elucidated by infrared, nuclear magnetic resonance, mass spectrometry and elemental analyses. The compounds were initially tested for their growth inhibitory activity using human breast and colon tumor cell lines. As summarized in Tables 1-3, compounds were identified that showed potent tumor cell activity with IC$_{50}$ values in the low nanomolar to the low micromolar range. Compounds 2f and 2j were among the most potent to inhibit tumor cell growth in the low nanomolar range. Testing compounds 2f and 2j in a large panel of human tumor cell lines showed that many were highly sensitive with IC$_{50}$ values less than 10 nM. Interestingly, compound 2f showed no cytotoxicity to normal human mammary epithelial cells (HMEC) up to a concentration of 10 µM, which may offer the potential for a large safety and selectivity index. Additionally, the multi-drug resistant tumor cell line (NCI/ADR-RES) was also highly sensitive to both compounds, which indicates the potential of this class of compounds to evade common mechanisms of drug resistance. The mechanism of action of these compounds appears to involve cGMP phosphodiesterase inhibition, although they possess unique properties compared with conventional PDE5 inhibitors, which do not have anticancer activity. The enabling feature of this class of compounds for the prevention or treatment of cancer was demonstrated by experiments showing strong in vivo antitumor activity of compound 2j in mice.

Experimental Section

All starting materials were commercially available and used without further purification. All reactions were carried out with the use of standard techniques under an inert atmosphere (N$_2$). The analytical thin-layer chromatography (TLC) was carried out on E. Merck 60-F254 pre-coated silica gel plates and components were usually visualized using UV light, Flash column chromatography was performed on silica gel 60 (E. Merck, 230-400 mesh). Melting points were determined on Buchi Melting Point apparatus and are uncorrected.

Proton NMR ($^1$H NMR) and carbon NMR ($^{13}$C NMR) spectra were recorded at ambient temperature on Varian Mercury VX-300 MHz spectrometer using tetramethylsilane as internal standard, and proton chemical shifts are expressed in ppm in the indicated solvent. The following abbreviations are used for multiplicity of NMR signals: s) singlet, brs) broad singlet, d) doublet, t) triplet, q) quadruplet, dd) double doublet, m) multiplet. The elemental analyses were performed by the Microanalytical Unit, Faculty of Science, Cairo University; and are within ±0.4% of the theoretical value, unless stated otherwise)

The following non-limiting examples further illustrate the present disclosure:

General procedure for the synthesis of Methyl 1-aryl-2,3,4,9-tetrahydro-1H-β-carboline-3-carboxylate (1a-r)

The appropriate tryptophan methyl ester (3.42 g, 15.7 mmol) and 2-bromo benzaldehyde, 2,5-dimethoxybenzaldehyde, 2,4-dichlorobenzaldehyde, 3,4-dichlorobenzaldehyde or 2,6-dichlorobenzaldehyde (17.25 mmol) were dissolved in CH$_2$Cl$_2$ (10 mL) and cooled to 0° C. in an ice bath. To this solution was added drop-wise TFA (1 mL), and the mixture was stirred at room temperature for 4 days. The reaction mixture was then basified with dilute NH$_4$OH solution and extracted with CH$_2$Cl$_2$ (3×10 mL). The organic layer was washed with water, brine, dried over anhydrous Na$_2$SO$_4$, filtered, and evaporated under reduced pressure. The residue was purified and the isomers were separated by column chromatography on silica gel eluting with CH$_2$Cl$_2$, to give first the appropriate cis-isomer followed by the trans-one. For the 2,6-dichlorobenzaldehyde, only the cis isomer was obtained and no chromatographic separation was carried out.

Example 1

(1R,3R) Methyl 1-(2-bromophenyl)-2,3,4,9-tetrahydro-1H-β-carboline-3-carboxylate (1a)

White solid; 33%; mp 105-106° C.; R$_f$=0.38 (CH$_2$Cl$_2$/MeOH 99:1); $^1$H-NMR (DMSO-d$_6$): δ 10.46 (s, 1H, NH), 7.7-7.68 (d, 1H, Ar), 7.46-7.43 (d, 1H, Ar), 7.33-7.20 (m, 4H, Ar), 7.04-6.93 (m, 2H, Ar), 5.64 (s, 1H, CHPh), 3.95-3.91 (m, 1H, CHCOOCH$_3$), 3.68 (s, 3H, OCH$_3$), 3.07-3.03 (dd, 1H, CH$_a$H$_b$), 2.89-2.75 (m, 1H, CH$_a$H$_b$); $^{13}$C-NMR (DMSO-d$_6$): δ 172.88, 140.75, 136.36, 134.16, 132.69, 130.74, 128.02, 126.44, 124.02, 120.94, 118.54, 117.70, 111.32, 107.65, 56.03 (C1), 51.89 (C3), 51.85, 25.26; MS: m/z 386 (M$^+$+2), m/z 384 (M$^+$, 100%); Anal. (C$_{19}$H$_{17}$BrN$_2$O$_2$) C, H, N.

Example 2

(1S,3R) Methyl 1-(2-bromophenyl)-2,3,4,9-tetrahydro-1H-β-carboline-3-carboxylate (1b)

White solid; 41%; mp 194-195° C.; R$_f$=0.15 (CH$_2$Cl$_2$/MeOH 99:1); $^1$H-NMR (DMSO-d$_6$): δ 10.73 (s, 1H, NH), 7.69-7.62 (m, 1H, Ar), 7.49-7.47 (d, 1H, Ar), 7.25-7.22 (m, 4H, Ar), 7.05-6.98 (m, 2H, Ar), 5.67 (s, 1H, CHPh), 3.68-3.63 (m, 4H, CHCOOCH$_3$+OCH$_3$), 3.14-3.08 (m, 1H, CH$_a$H$_b$), 2.90-2.87 (dd, 1H, CH$_a$H$_b$); $^{13}$C-NMR (DMSO-d$_6$): δ 173.53, 141.11, 136.2, 132.93, 130.37, 129.53, 127.47, 126.35, 124.09, 121.12, 118.51, 117.81, 111.19, 107.86, 53.69 (C1), 51.83 (C3), 51.36, 24.89; MS: m/z 386 (M$^+$+2), m/z 384 (M$^+$, 100%); Anal. (C$_{19}$H$_{17}$BrN$_2$O$_2$) C, H, N.

Example 3

(1S,3S) Methyl 1-(2-bromophenyl)-2,3,4,9-tetrahydro-1H-β-carboline-3-carboxylate (1c)

White solid; 40%; mp 104-105° C.; R$_f$=0.39 (CH$_2$Cl$_2$/MeOH 99:1); $^1$H-NMR (DMSO-d$_6$): δ 10.46 (s, 1H, NH), 7.70-7.67 (d, 1H, Ar), 7.46-7.43 (d, 1H, Ar), 7.33-7.20 (m, 5H, Ar+NH), 7.04-6.93 (m, 2H, Ar), 5.64 (s, 1H, CHPh), 3.93 (m, 1H, CHCOOCH$_3$), 3.68 (s, 3H, OCH$_3$), 3.07-3.03 (dd, 1H, CH$_a$H$_b$), 2.90-2.80 (m, 1H, CH$_a$H$_b$); $^{13}$C-NMR (DMSO-d$_6$): δ 172.80, 136.36, 134.07, 132.64, 130.74, 129.83, 128.01, 126.43, 124.02, 120.93, 118.52, 117.67, 115.92, 111.30, 107.63, 56.61 (C1), 51.85 (C3), 25.20; MS: m/z 386 (M$^+$+2), m/z 384 (M$^+$, 100%); Anal. (C$_{19}$H$_{17}$BrN$_2$O$_2$) C, H, N.

Example 4

(1R,3S) Methyl 1-(2-bromophenyl)-2,3,4,9-tetrahydro-1H-β-carboline-3-carboxylate (1d)

White solid; 28%; mp 193-195° C.; R$_f$=0.14 (CH$_2$Cl$_2$/MeOH 99:1); $^1$H-NMR (DMSO-d$_6$): δ 10.71 (s, 1H, NH), 7.69-7.67 (t, 1H, Ar), 7.48-7.46 (d, 1H, Ar), 7.24-7.21 (d, 3H, Ar), 7.07-6.95 (m, 2H, Ar), 6.76-6.5 (m, 1H, Ar), 5.66 (s, 1H, CHPh), 3.67-3.62 (m, 4H, CHCOOCH$_3$+OCH$_3$), 3.13-3.07 (m, 1H, CH$_a$H$_b$), 2.89-2.80 (dd, 1H, CH$_a$H$_b$); $^{13}$C-NMR (DMSO-d$_6$): δ 173.51, 141.10, 136.19, 132.91, 130.35, 129.50, 127.45, 126.34, 124.06, 121.09, 118.48, 117.77, 111.16, 107.83, 53.64 (C1), 51.79 (C3), 51.35, 24.89; m/z 386 (M$^+$+2), m/z 384 (M$^+$, 100%); Anal. (C$_{19}$H$_{17}$BrN$_2$O$_2$) C, H, N.

Example 5

(1R,3R) Methyl 1-(2,5-dimethoxyphenyl)-2,3,4,9-tetrahydro-1H-β-carboline-3-carboxylate (1e)

Buff solid; 25%; mp 102-105° C.; R$_f$ 0.39 (CH$_2$Cl$_2$/MeOH 98:2); $^1$H-NMR (DMSO-d$_6$): δ 7.79 (brs, 1H, NH), 7.53-7.50 (d, 1H, Ar), 7.25-6.82 (m, 6H, Ar), 5.71 (s, 1H, CHPh), 4.02-3.97 (m, 1H, CHCOOCH$_3$), 3.87 (s, 3H, OCH$_3$), 3.83 (s, 3H, OCH$_3$), 3.71 (s, 3H, OCH$_3$), 3.37-3.17 (m, 1H, CHaH$_b$), 3.05-3.00 (m, 1H, CH$_a$Hb). $^{13}$C-NMR (DMSO-d$_6$): δ 173.1, 154.1, 151.3, 135.9, 134.5, 127.1, 121.6, 119.4, 117.9, 114.7, 114.1, 112.2, 110.9, 108.2, 56.9, 56.4, 55.8 (C1), 52.2 (C3), 52.0, 25.4; MS: m/z 366 (M$^+$, 100%); Anal (C$_{21}$H$_{22}$N$_2$O$_4$) C, H, N.

Example 6

(1S,3R) Methyl 1-(2,5-dimethoxyphenyl)-2,3,4,9-tetrahydro-1H-β-carboline-3-carboxylate (1f)

Yellow solid; 45%; mp 139-142° C.; R$_f$: 0.18 (CH$_2$Cl$_2$/MeOH 98:2); $^1$H-NMR (DMSO-d$_6$): δ 7.93 (s, 1H, NH), 7.56-7.53 (d, 1H, Ar), 7.25-6.62 (m, 6H, Ar), 5.81 (s, 1H, CHPh), 3.97-3.95 (m, 1H, CHCOOCH$_3$), 3.93 (s, 3H, OCH$_3$), 3.75 (s, 3H, OCH$_3$), 3.66 (s, 3H, OCH$_3$), 3.28-3.21 (dd, 1H, CHaH$_b$), 3.10-3.02 (m, 1H, CH$_a$Hb), $^{13}$C-NMR (DMSO-d$_6$): δ 173.8, 153.5, 151, 136.3, 132.4, 127.8, 126.9, 125.8, 121.8, 119.2, 118, 115.8, 112.6, 111.5, 108.5, 56.0, 55.7, 52.4, 52.2 (C1), 49.4 (C3), 29.7; MS: m/z 366 (M$^+$, 100%); Anal. (C$_{21}$H$_{22}$N$_2$O$_4$) C, H, N.

Example 7

(1S,3S) Methyl 1-(2,5-dimethoxyphenyl)-2,3,4,9-tetrahydro-1H-β-carboline-3-carboxylate (1g)

Yellow solid; 25%; mp 100-102° C.; R$_f$ 0.38 (CH$_2$Cl$_2$/MeOH 98:2); $^1$H-NMR (DMSO-d$_6$): δ 7.78 (s, 1H, NH), 7.53-7.51 (d, 1H, Ar), 7.27-6.82 (m, 6H, Ar), 5.69 (s, 1H, CHPh), 4.02-3.97 (dd, 1H, CHCOOCH$_3$), 3.88 (s, 3H, OCH$_3$), 3.83 (s, 3H, OCH$_3$), 3.71 (s, 3H, OCH$_3$), 3.25-3.18 (m, 1H, CHaH$_b$), 2.95-3.05 (m, 1H, CH$_a$Hb); $^{13}$C-NMR (DMSO-d$_6$): δ 173.1, 154.2, 151.3, 135.9, 134.4, 127, 121.6, 119.4, 117.9, 114.7, 114.1, 112.3, 110.8, 108.1, 56.9, 56.4, 55.8 (C1), 52.2 (C3), 52, 25.5; MS: m/z 366 (M$^+$, 100%); Anal. (C$_{21}$H$_{22}$N$_2$O$_4$) C, H, N.

Example 8

(1R,3S) Methyl 1-(2,5-dimethoxyphenyl)-2,3,4,9-tetrahydro-1H-β-carboline-3-carboxylate (1h)

Yellow solid; 45%; mp 138-141° C.; R$_f$: 0.17 (CH$_2$Cl$_2$/MeOH 98:2); $^1$H-NMR (DMSO-d$_6$): δ 7.96 (brs, 1H, NH), 7.56-7.53 (m, 1H, Ar), 7.18-6.61 (m, 6H, Ar), 5.82 (s, 1H, CHPh), 3.98-3.96 (m, 1H, CHCOOCH$_3$), 3.920 (s, 3H, OCH$_3$), 3.75 (s, 3H, OCH$_3$), 3.66 (s, 3H, OCH$_3$), 3.29-3.22 (m, 1H, CHaH$_b$), 3.04-3.12 (m, 1H, CH$_a$Hb), $^{13}$C-NMR (DMSO-d$_6$): δ 173.9, 153.5, 151.1, 136.1, 132.8, 131.5, 126.9, 121.7, 119.2, 118, 115.6, 112.5, 111.6, 110.9, 108.7, 56.1, 55.7, 52.5, 52.0 (C1), 49.1 (C3), 24.9; MS: m/z 366 (M$^+$, 100%); Anal. (C$_{21}$H$_{22}$N$_2$O$_4$) C, H, N.

Example 9

(1R,3R) Methyl-1-(2,4-dichlorophenyl)-2,3,4,9-tetrahydro-1H-β-carboline-3-carboxylate (1i)

Yellow powder; 35%; m.p: 88-92° C.; R$_f$=0.19 (CH$_2$Cl$_2$); IR (cm$^{-1}$): 3406 (—NH—), 1734 (—CO—); $^1$H-NMR: δ 7.48 (s, 1H, NH), 7.51 (d, 1H, J=7.0 Hz, Ar), 7.35 (d, 1H, J=7.0 Hz, Ar), 7.26-7.15 (m, 4H, Ar+NH), 7.04-6.93 (m, 2H, Ar), 5.82 (s, 1H, CHPh), 4.03-4.00 (m, 1H, CHCOOCH$_3$), 3.83 (s, 3H, OCH$_3$), 3.25 (dd, 1H, J=4.3/7.0 Hz, CH$_a$H$_b$), 3.23-3.04 (m, 1H, CH$_a$H$_b$); $^{13}$C-NMR: δ 172.82, 136.16, 135.01, 134.11, 132.10, 131.23, 130.02, 128.06, 126.81, 123.40, 122.26, 119.83, 118.28, 110.97, 109.33, 56.55 (C1), 54.53, 52.40 (C3), 25.28; MS: m/z 378 (M$^+$+4), m/z 376 (M$^+$+2), m/z 374 (M$^+$), m/z 217 (100%); Anal. ($C_{19}H_{16}Cl_2N_2O_2$), C, H, N.

Example 10

(1S,3R) Methyl 1-(2,4-dichlorophenyl)-2,3,4,9-tetrahydro-1H-β-carboline-3-carboxylate (1j)

Yellow powder; 34%; m.p: 130-133° C.; $R_f$=0.12 ($CH_2Cl_2$); IR (cm$^{-1}$): 3388 (—NH—), 1735 (—CO—); $^1$H-NMR: δ 7.64 (s, 1H, NH), 7.56 (d, 1H, J=7.0 Hz, Ar), 7.47 (s, 1H, NH), 7.00 (d, 1H, J=7.0 Hz, Ar), 7.27-7.12 (m, 5H, Ar), 5.97 (s, 1H, CHPh), 3.92-3.88 (m, 1H, CHCOOCH$_3$), 3.74 (s, 3H, OCH$_3$), 3.30 (dd, 1H, J=4.6/7.6 Hz, CH$_a$H$_b$), 3.17-3.15 (m, 1H, CH$_a$H$_b$); $^{13}$C-NMR: δ 173.09, 137.15, 136.29, 134.73, 134.51, 131.16, 130.83, 129.78, 127.27, 126.63, 122.48, 119.82, 118.38, 111.08, 109.43, 52.40 (C1), 52.27, 51.15 (C3), 24.39; MS: m/z 378 (M$^+$+4), m/z 376 (M$^+$+2), m/z 374 (M$^+$, 100%); Anal. ($C_{19}H_{16}Cl_2N_2O_2$), C, H, N.

Example 11

(1S,3S)Methyl 1-(2,4-dichlorophenyl)-2,3,4,9-tetrahydro-1H-β-carboline-3-carboxylate (1k)

White powder; 45%; m.p: 90-92° C.; $R_f$=0.19 ($CH_2Cl_2$); IR (cm$^{-1}$): 3433 (—NH—), 1728 (—CO—); $^1$H NMR: δ 7.90 (s, 1H, NH), 7.54-7.43 (m, 2H, Ar), 7.38 (d, 1H, J=7.2 Hz, Ar), 7.26-7.10 (m, 5H, Ar+NH), 5.8 (s, 1H, CHPh), 3.90-3.87 (m, 1H, CHCOOCH$_3$), 3.82 (s, 3H, OCH$_3$), 3.25 (dd, 1H, J=4.3/7.6 Hz, CHaH$_b$), 3.01-2.90 (m, 1H, CH$_a$Hb); $^{13}$C-NMR: δ 172.90, 136.15, 135.10, 134.65, 133.15, 132.12, 131.45, 130.0, 129.38, 128.04, 126.85, 122.01, 119.8, 115.92, 110.96, 109.37, 56.57 (C1), 51.36 (C3), 25.38; MS: m/z 378 (M$^+$+4), m/z 376 (M$^+$+2), m/z 374 (M+, 100%); Anal. ($C_{19}H_{16}Cl_2N_2O_2$).

Example 12

(1R,3S)Methyl 1-(2,4-dichlorophenyl)-2,3,4,9-tetrahydro-1H-β-carboline-3-carboxylate (1l)

White powder; 30%; m.p: 128-130° C.; $R_f$=0.12 ($CH_2Cl_2$); IR (cm$^{-1}$): 3396 (—NH—), 1739 (—CO—); $^1$H NMR: δ 7.80 (s, 1H, NH), 7.49 (s, 1H, NH), 7.46 (d, 1H, J=7.2 Hz, Ar), 7.19-7.11 (m, 5H, Ar), 6.94 (d, 1H, J=7.0 Hz, Ar), 5.30 (s, 1H, CHPh), 3.74 (s, 3H, OCH$_3$), 3.68-3.62 (m, 1H, CHCOOCH$_3$), 3.30 (dd, 1H, J=4.6/7.6 Hz, CHaH$_b$), 3.16-3.14 (m, 1H, CH$_a$Hb); $^{13}$C-NMR: δ 173.17, 136.27, 134.70, 134.50, 131.12, 131.0, 129.77, 127.27, 126.65, 122.46, 120.01, 119.82, 118.39, 111.06, 109.46, 52.38 (C1), 51.28 (C3), 51.14; MS: m/z 378 (M$^+$+4), m/z 376 (M$^+$+2), m/z 374 (M+, 100%); Anal. ($C_{19}H_{16}Cl_2N_2O_2$), C, H, N.

Example 13

(1R,3R) Methyl-1-(3,4-dichlorophenyl)-2,3,4,9-tetrahydro-1H-β-carboline-3-carboxylate (1m)

Yellow powder; 35%; mp: 90-92° C.; $R_f$=0.15 ($CH_2Cl_2$); IR (cm$^{-1}$): 3396 (—NH—), 1734 (—CO—); $^1$H NMR: δ 9.0 (s, 1H, NH), 7.51-7.44 (m, 5H, Ar+NH), 7.25 (d, 1H, J=7.2 Hz, Ar), 7.20-7.10 (m, 2H, Ar), 5.23 (s, 1H, CHPh), 3.96 (dd, J=4.0/7.6 Hz, 1H, CH$_a$H$_b$), 3.82 (s, 3H, OCH$_3$), 3.05-3.01 (m, 1H, CHCOOCH$_3$), 3.00-2.95 (m, 1H, CH$_a$H$_b$); $^{13}$C-NMR: δ 172.88, 140.98, 136.25, 133.30, 133.12, 132.74, 130.92, 130.58, 127.94, 126.90, 122.35, 119.89, 118.37, 111.03, 109.34, 57.73 (C1), 56.64, 52.42 (C3), 25.43; MS: m/z 378 (M$^+$+4), m/z 376 (M$^+$+2), m/z 374 (M$^+$, 100%); Anal.; [α]$^{20}_D$=+58.35 (c=0.1, EtOH).

Example 14

(1S,3R) Methyl-1-(3,4-dichlorophenyl)-2,3,4,9-tetrahydro-1H-β-carboline-3-carboxylate (1n)

Yellow powder; 20%; m.p: 140-143° C.; $R_f$=0.10 ($CH_2Cl_2$); IR (cm$^{-1}$): 3345 (—NH—), 1710 (—CO—); $^1$HNMR: δ 7.55 (d, 1H, J=7.2 Hz, Ar), 7.50-7.02 (m, 3H, Ar), 7.20-7.10 (m, 5H, Ar), 5.49 (s, 1H, CHPh), 3.98-3.95 (m, 1H, CHCOOCH$_3$), 3.73 (s, 3H, OCH$_3$), 3.37 (d, 1H, J=8.0 Hz, CH$_a$H$_b$), 3.29 (dd, 1H, J=4.6/8.0 Hz, CH$_a$H$_b$); $^{13}$C-NMR: δ 172.87, 148.02, 136.27, 135.02, 132.95, 132.55, 130.72, 130.57, 128.02, 126.69, 122.51, 119.85, 118.45, 111.09, 108.57, 53.94 (C1), 52.59 (C3), 52.40, 24.17; MS: m/z 378 (M$^+$+4), m/z 376 (M$^+$+2), m/z 374 (M$^+$, 100%); Anal.; [α]$^{20}_D$=+69.5 (c=0.1, EtOH).

Example 15

(1S,3S) Methyl-1-(3,4-dichlorophenyl)-2,3,4,9-tetrahydro-1H-β-carboline-3-carboxylate (1o)

Yellow powder; 38%; m.p: 88-91° C.; $R_f$=0.15 ($CH_2Cl_2$); IR (cm$^{-1}$): 3395 (—NH—), 1734 (—CO—); $^1$H NMR: δ 7.51-7.44 (m, 5H, Ar+NH), 7.25 (d, 1H, J=7.2 Hz, Ar), 7.20-7.10 (m, 2H, Ar), 5.24 (s, 1H, CHPh), 3.95 (dd, 1H, J=4.0/8.0 Hz, CHCOOCH$_3$), (s, 3H, OCH$_3$), 3.25 (dd, 1H, J=4.6/7.6 Hz, CH$_a$H$_b$) 3.05-2.95 (m, 1H, CH$_a$H$_b$); $^{13}$C-NMR: δ 172.78, 140.81, 136.27, 133.16, 133.12, 132.78, 130.919, 130.62, 127.99, 127.51, 126.88, 122.37, 119.90, 118.37, 111.04, 109.32, 57.70 (C1), 52.42 (C3), 25.36; MS: m/z 378 (M$^+$+4), m/z 376 (M$^+$+2), m/z 374 (M$^+$, 100%); Anal. ($C_{19}H_{16}Cl_2N_2O_2$), C, H, N; [α]$^{20}_D$=58.35 (c=0.1, EtOH).

Example 16

(1R,3S)Methyl-1-(3,4-dichlorophenyl)-2,3,4,9-tetrahydro-1H-β-carboline-3-carboxylate (1p)

Yellow powder; 25%; m.p: 139-142° C.; $R_f$=0.10 ($CH_2Cl_2$); IR (cm$^{-1}$): 3386 (—NH—), 1731 (—CO—); $^1$H NMR: δ 7.55 (d, 2H, J=7.0 Hz, Ar+NH), 7.40-7.35 (m, 3H, Ar+NH), 7.27 (d, 2H, J=7.0 Hz, Ar), 7.21-7.10 (m, 2H, Ar), 5.45 (s, 1H, CHPh), 3.97-3.93 (m, 1H, CHCOOCH$_3$), 3.73 (s, 3H, OCH$_3$), 3.31-2.26 (m, 1H, CH$_a$H$_b$), 3.18 (dd, 1H, J=4.6/8.0 Hz, CH$_a$H$_b$); $^{13}$C-NMR: δ 173.13, 139.96, 136.04, 135.80, 132.57, 130.45, 130.22, 129.07, 128.84, 126.98, 124.06, 121.91, 119.77, 118.01, 110.99, 108.63, 53.20 (C1), 52.36 (C3), 25.72; MS: m/z 378 (M$^+$+4), m/z 376 (M$^+$+2), m/z 374 (M$^+$, 100%); Anal. ($C_{19}H_{16}Cl_2N_2O_2$), C, H, N; [α]$^{20}_D$=−69.5 (c=0.1, EtOH).

Example 17

(1R,3R) Methyl 1-(2,6-dichlorophenyl)-2,3,4,9-tetrahydro-1H-β-carboline-3 carboxylate (1q)

Red powder; 55%; m.p: 102-105° C.; $R_f$=0.13 (100% $CH_2Cl_2$); IR (cm$^{-1}$): 3389 (—NH—), 1729 (—CO—); $^1$H-NMR: δ 7.58-7.52 (m, 3H, Ar+NH), 7.28-7.27 (m, 3H, Ar+NH), 7.26-7.25 (m, 3H, Ar), 6.29 (s, 1H, CHPh), 4.14-4.06 (m, 1H, CHCOOCH$_3$), 3.85 (s, 3H, OCH$_3$), 3.32 (dd, 1H, J=4.0/8.0 Hz, CH$_a$H$_b$), 3.03-2.99 (m, 1H, CH$_a$H$_b$); $^{13}$C-NMR: δ 172.25, 138.07, 136.20, 135.88, 134.37, 130.47, 129.40, 127.84, 126.60, 121.82, 119.66, 118.07, 112.06, 111.02, 56.83 (C1), 54.07, 52.21 (C3), 37.04, 27.15; MS: m/z 378 (M$^+$+4), m/z 376 (M$^+$+2), m/z 374 (M$^+$), m/z 217 (100%); Anal. (C$_{19}$H$_{16}$Cl$_2$N$_2$O$_2$), C, H, N.

Example 18

(1S,3S) Methyl 1-(2,6-dichlorophenyl)-2,3,4,9-tetrahydro-1H-β-carboline-3-carboxylate (1r)

Red powder; 57%; m.p: 101-103° C.; R$_f$=0.13 (100% CH$_2$Cl$_2$); IR (cm$^{-1}$): 3386 (—NH—), 1730 (—CO—); $^1$H-NMR: δ 7.51-7.50 (m, 3H, Ar+NH), 7.43 (d, 1H, J=7.2 Hz, Ar), 7.26-7.25 (m, 3H, Ar+NH), 7.13-7.11 (m, 2H, Ar), 6.21 (s, 1H, CHPh), 4.07-4.04 (m, 1H, CHCOOCH$_3$), 3.83 (s, 3H, OCH$_3$), 3.25 (dd, 1H, J=4.0/8.0 Hz, CH$_a$H$_b$), 2.99-2.96 (m, 1H, CH$_a$H$_b$); $^{13}$C-NMR: δ 173.13, 136.96, 135.80, 134.3, 132.57, 130.46, 129.08, 128.84, 126.98, 121.91, 119.77, 118.01, 110.99, 108.64, 57.21 (C1), 54.21, 52.36 (C3), 36.88, 25.72; MS: m/z 378 (M$^+$+4), m/z 376 (M$^+$+2), m/z 374 (M$^+$, 100%); Anal. (C$_{19}$H$_{16}$Cl$_2$N$_2$O$_2$), C, H, N.

General procedure for Methyl 1-aryl-2-(2-chloroacetyl)-2,3,4,9-tetrahydro-1H-β-carboline-3-carboxylate (2a-r)

To a stirred solution of the appropriate β-carboline 1a-r (5.7 mmol) and NaHCO$_3$ (6.89 mmol) in CHCl$_3$ (40 mL) chloroacetyl chloride (1.09 mL, 13.69 mmol) was added dropwise under ice cooling. The mixture was then stirred at room temperature for 2 hours. The mixture was diluted with CH$_2$Cl$_2$, and washed with a solution of NaHCO$_3$. The organic layer was dried over Na$_2$SO$_4$ and evaporated under reduced pressure. The residue was subjected to column chromatography using CH$_2$Cl$_2$ as an eluent, then recrystallized from ethanol.

Example 19

Methyl (1R,3R)-1-(2-bromophenyl)-2-(2-chloroacetyl)-2,3,4,9-tetrahydro-1H-β-carboline-3-carboxylate (2a)

White solid; 88%; mp 113-115° C.; R$_f$=0.68 (CH$_2$Cl$_2$/MeOH 99:1); $^1$H-NMR (CDCl$_3$): δ 8.00 (br s, 1H, NH), 7.88-7.85 (d, 1H, Ar), 7.57-7.54 (d, 1H, Ar), 7.31-7.14 (m, 6H, Ar), 6.73 (s, 1H, CHPh), 5.18-5.14 (m, 1H, CHCOOCH$_3$), 4.19-4.15 (m, 2H, COCH$_2$Cl), 3.64 (br s, 3H, OCH$_3$), 3.37-3.28 (m, 2H, CH$_2$); MS: m/z 462 (M$^+$+2), m/z 460 (M$^+$), m/z 385 (100%); Anal. (C$_{21}$H$_{18}$BrClN$_2$O$_3$). C, H, N

Example 20

Methyl (1S,3R)-1-(2-bromophenyl)-2-(2-chloroacetyl)-2,3,4,9-tetrahydro-1H-β-carboline-3-carboxylate (2b)

White solid; 74%; mp 132-135° C.; R$_f$=0.58 (CH$_2$Cl$_2$/MeOH 99:1); $^1$H-NMR (CDCl$_3$): δ 8.22 (s, 1H, NH), 7.61-7.50 (m, 2H, Ar), 7.28-7.08 (m, 6H, Ar), 6.65 (s, 1H, CHPh), 5.31 (br s, 1H, CHCOOCH$_3$), 4.19-4.06 (m, 2H, COCH$_2$Cl), 3.82-3.72 (m, 5H, OCH$_3$+CH$_2$); MS: m/z 462 (M$^+$+2), m/z 460 (M$^+$), m/z 383 (100%); Anal. (C$_{21}$H$_{18}$BrClN$_2$O$_3$). C, H, N.

Example 21

Methyl (1S,3S)-1-(2-bromophenyl)-2-(2-chloroacetyl)-2,3,4,9-tetrahydro-1H-β-carboline-3-carboxylate (2c)

White solid; 83%; mp 112-113° C.; R$_f$=0.68 (CH$_2$Cl$_2$/MeOH 99:1); $^1$H-NMR (CDCl$_3$): δ 7.97 (br s, 1H, NH), 7.68-7.65 (d, 1H, Ar), 7.57-7.54 (d, 1H, Ar), 7.31-7.12 (m, 6H, Ar), 6.73 (s, 1H, CHPh), 5.18-5.14 (m, 1H, CHCOOCH$_3$), 4.19-4.15 (m, 2H, COCH$_2$Cl), 3.64 (br s, 3H, OCH$_3$), 3.37-3.26 (m, 2H, CH$_2$); MS: m/z 462 (M$^+$+2), m/z 460 (M$^+$), m/z 383 (100%); Anal. (C$_{21}$H$_{18}$BrClN$_2$O$_3$). C, H, N.

Example 22

Methyl (1R,3S)-1-(2-bromophenyl)-2-(2-chloroacetyl)-2,3,4,9-tetrahydro-1H-β-carboline-3-carboxylate (2d)

White solid; 81%; mp 132-133° C.; R$_f$=0.60 (CH$_2$Cl$_2$/MeOH 99:1); $^1$H-NMR (CDCl$_3$): δ 8.22 (s, 1H, NH), 7.62-7.50 (m, 2H, Ar), 7.29-7.08 (m, 6H, Ar), 6.65 (s, 1H, CHPh), 5.31 (br s, 1H, CHCOOCH$_3$), 4.19-4.06 (m, 2H, COCH$_2$Cl), 3.74-3.65 (m, 5H, OCH$_3$+CH$_2$); MS: m/z 462 (M$^+$+2), m/z 460 (M$^+$), m/z 385 (100%); Anal. (C$_{21}$H$_{18}$BrClN$_2$O$_3$). C, H, N.

Example 23

Methyl (1R,3R)-1-(2,5-dimethoxyphenyl)-2-(2-chloroacetyl)-2,3,4,9-tetrahydro-1H-β-carboline-3-carboxylate (2e)

White solid; 85%; mp 108-111° C.; R$_f$=0.66 (CH$_2$Cl$_2$/MeOH 99:1); $^1$H-NMR (CDCl$_3$): δ8.08 (br s, 1H, NH), 7.56-7.54 (d, 1H, Ar), 7.31-7.28 (m, 2H, Ar), 7.27-7.13 (m, 2H, Ar), 6.93-6.91 (d, 1H, Ar), 6.82-6.80 (m, 2H, Ar), 6.79 (brs, 1H, CHPh), 5.33 (brs, 1H, CHCOOCH$_3$), 4.28 (brs, 2H, COCH$_2$Cl), 3.98 (s, 3H, OCH$_3$), 3.69 (s, 3H, OCH$_3$), 3.50 (s, 3H, OCH$_3$), 3.44-3.19 (m, 2H, CH$_2$); MS: m/z 442 (M$^+$), m/z 365 (100); Anal. (C$_{23}$H$_{23}$ClN$_2$O$_5$). C, H, N.

Example 24

Methyl (1S,3R)-1-(2,5-dimethoxyphenyl)-2-(2-chloroacetyl)-2,3,4,9-tetrahydro-1H-β-carboline-3-carboxylate (2f)

White solid; 89%; mp 232-232° C.; R$_f$=0.49 (CH$_2$Cl$_2$/MeOH 99:1); $^1$H-NMR (CDCl$_3$): δ8.26 (br s, 1H, NH), 7.51-7.48 (d, 1H, Ar), 7.27-7.24 (m, 2H, Ar), 7.17-7.12 (m, 2H, Ar), 6.96 (brs, 1H, Ar), 6.81-6.79 (m, 1H, Ar), 6.60 (brs, 1H, CHPh), 5.52 (brs, 1H, CHCOOCH$_3$), 4.23 (s, 2H, COCH$_2$Cl), 4.05 (s, 3H, OCH$_3$), 3.69 (s, 3H, OCH$_3$), 3.64 (s, 3H, OCH$_3$), 3.42-3.10 (m, 2H, CH$_2$); MS: m/z 442 (M$^+$), m/z 365 (100); Anal. (C$_{23}$H$_{23}$ClN$_2$O$_5$). C, H, N.

Example 25

Methyl (1S,3S)-1-(2,5-dimethoxyphenyl)-2-(2-chloroacetyl)-2,3,4,9-tetrahydro-1H-β-carboline-3-carboxylate (2g)

White solid; 83%; mp 105-108° C.; $R_f$=0.65 ($CH_2Cl_2$/MeOH 99:1); $^1$H-NMR ($CDCl_3$): δ 8.05 (br s, 1H, NH), 7.56-7.54 (d, 1H, Ar), 7.27-7.14 (m, 4H, Ar), 6.94-6.91 (d, 1H, Ar), 6.82-6.80 (m, 1H, Ar), 6.58 (brs, 1H, CHPh), 5.38 (brs, 1H, CHCOOCH$_3$), 4.52 (brs, 2H, COCH$_2$Cl), 4.05 (s, 3H, OCH$_3$), 3.66 (s, 3H, OCH$_3$), 3.51 (s, 3H, OCH$_3$), 3.45-3.25 (m, 2H, CH$_2$); MS: m/z 442 (M$^+$), m/z 365 (100); Anal. ($C_{23}H_{23}ClN_2O_5$). C, H, N.

Example 26

Methyl (1R,3S)-1-(2,5-dimethoxyphenyl)-2-(2-chloroacetyl)-2,3,4,9-tetrahydro-4H-β-carboline-3-carboxylate (2h)

White solid; 88%; mp 228-230° C.; $R_f$=0.49 ($CH_2Cl_2$/MeOH 99:1); $^1$H-NMR ($CDCl_3$): δ 8.24 (br s, 1H, NH), 7.51-7.48 (d, 1H, Ar), 7.27-1-7.25 (m, 2H, Ar), 7.23-7.12 (m, 2H, Ar), 6.93-6.91 (d, 1H, Ar), 6.82-6.80 (m, 1H, Ar), 6.61 (brs, 1H, 1H, CHPh), 5.53 (brs, 1H, CHCOOCH$_3$), 4.23 (brs, 2H, COCH$_2$Cl), 4.06 (s, 3H, OCH$_3$), 3.69 (s, 3H, OCH$_3$), 3.64 (s, 3H, OCH$_3$), 3.40-3.19 (m, 2H, CH$_2$); MS: m/z 442 (M$^+$), m/z 365 (100). Anal. ($C_{23}H_{23}ClN_2O_5$). C, H, N.

Example 27

(1R,3R) Methyl 1-(2,4-dichlorophenyl)-2-(2-chloroacetyl)-2,3,4,9-tetrahydro-1H-β-carboline-3-carboxylate (2i)

Orange powder; 78%; m.p: 215-218° C.; $R_f$=0.53 ($CH_2Cl_2$); IR (cm$^{-1}$): 3294 (—NH—), 1731, 1666 (—CO—); $^1$H-NMR: δ 7.50 (s, 1H, NH), 7.30-7.16 (m, 7H, Ar), 6.63 (s, 1H, CHPh), 4.53 (s, 1H, CHCOOCH$_3$), 4.20-4.15 (m, 2H, COCH$_2$Cl), 3.64 (s, 3H, OCH$_3$), 3.43-3.39 (m, 2H, CH$_2$); MS: m/z 454 (M$^+$+4), m/z 452 (M$^+$+2), m/z 450 (M$^+$), m/z 373 (100%); Anal. ($C_{21}H_{17}Cl_3N_2O_3$), C, H, N.

Example 28

(1S,3R) Methyl 1-(2,4-dichlorophenyl)-2-(2-chloroacetyl)-2,3,4,9-tetrahydro-1H-β-carboline-3-carboxylate (2j)

Green powder; 80%; m.p: 106-109° C.; $R_f$=0.37 (100% $CH_2Cl_2$); IR (cm$^{-1}$): 3370 (—NH—), 1739, 1668 (—CO—); $^1$H-NMR: δ 8.08 (s, 1H, NH), 7.51 (d, 1H, J=7.2, Ar), 7.28-7.11 (m, 6H, Ar), 6.57 (s, 1H, CHPh), 5.30 (br s, 1H, CHCOOCH$_3$), 4.18-4.10 (m, 2H, COCH$_2$Cl), 3.64 (s, 3H, OCH$_3$), 3.53-3.49 (m, 2H, CH$_2$); MS: m/z 454 (M$^+$+4), m/z 452 (M$^+$+2), m/z 450 (M$^+$), m/z 373 (100%); Anal. ($C_{21}H_{17}Cl_3N_2O_3$), C, H, N.

Example 29

(1S,3S) Methyl 1-(2,4dichlorophenyl)-2-(2-chloroacetyl)-2,3,4,9-tetrahydro-1H-β-carboline-3-carboxylate (2k)

White powder; 88%; m.p: 215-218° C.; $R_f$=0.52 ($CH_2Cl_2$); IR (cm$^{-1}$): 3315 (—NH—), 1737, 1664 (—CO—); $^1$H NMR: δ 7.50 (brs, 1H, NH), 7.26-7.15 (m, 7H, Ar), 6.57 (s, 1H, CHPh), 4.52 (s, 1H, CHCOOCH$_3$), 4.20-4.15 (m, 2H, COCH$_2$Cl), 3.63 (br s, 3H, OCH$_3$), 3.49-3.48 (m, 2H, CH$_2$); MS: m/z 454 (M$^+$+4), m/z 452 (M$^+$+2), m/z 450 (M$^+$, 100%); Anal. ($C_{21}H_{17}Cl_3N_2O_3$), C, H, N.

Example 30

(1R,3S) Methyl 1-(2,4-dichlorophenyl)-2-(2-chloroacetyl)-2,3,4,9-tetrahydro-1H-β-carboline-3-carboxylate (2l)

White powder; 75%; m.p: 109-112° C.; $R_f$=0.37 ($CH_2Cl_2$); IR (cm$^{-1}$): 3347 (—NH—), 1739 (—CO—), 1668 (—CO—); $^1$H NMR: δ 7.80 (brs, 1H, NH), 7.39 (d, 1H, J=8.0 Hz, Ar), 7.18-7.12 (m, 6H, Ar), 6:54 (s, 1H, CHPh), 5.56 (d, 1H, J=7.0 Hz, CHCOOCH$_3$), 3.95-393 (m, 2H, COCH$_2$Cl), 3.72 (s, 3H, OCH$_3$), 3.31 (dd, 1H, J=3.6/7.6 Hz, CH$_a$CH$_b$), 3.18 (dd, 1H, J=3.6/7.6 Hz, CH$_a$CH$_b$); MS: m/z 454 (M$^+$+4), m/z 452 (M$^+$+2), m/z 450 (M$^+$), m/z 373 (100%); Anal. ($C_{21}H_{17}C_{13}N_2O_3$), C, H, N.

Example 31

(1R,3R) Methyl 1-(3,4-dichlorophenyl)-2-(2-chloroacetyl)-2,3,4,9-tetrahydro-1H-β-carboline-3-carboxylate (2m)

White powder; 86%; m.p: 283-285° C.; $R_f$=0.47 ($CH_2Cl_2$); IR (cm$^{-1}$): 3283 (—NH—), 1737 (—CO—), 1662 (—CO—); $^1$H NMR: δ 8.9 (s, 1H, NH), 7.60 (d, 2H, J=7.6 Hz, Ar), 7.32-7.16 (m, 5H, Ar), 6.83 (s, 1H, CHPh), 4.99 (d, 1H, J=7.0 Hz, CHCOOCH$_3$), 4.35 (m, COCH$_2$Cl), 4.22 (dd, 1H, J=3.6/7.6 Hz, CH$_a$CH$_b$), 3.70 (dd, 1H, J=3.6/7.6 Hz, CH$_a$CH$_b$), 3.49 (s, 3H, OCH$_3$); MS: m/z 454 (M$^+$+4), m/z 452 (M$^+$+2), m/z 450 (M$^+$, 100%); Anal. ($C_{21}H_{17}Cl_3N_2O_3$), C, H, N.

Example 32

(1S,3R) Methyl 1-(3,4dichlorophenyl)-2-(2-chloroacetyl)-2,3,4,9-tetrahydro-1H-β-carboline-3-carboxylate (2n)

White powder; 79%; m.p: 163-165° C.; $R_f$=0.22 ($CH_2Cl_2$); IR (cm$^{-1}$): 3387 (—NH—), 1734 (—CO—), 1663 (—CO—); $^1$H NMR: δ 8.9 (s, 1H, NH), 7.77 (d, 2H, J=8.2 Hz, Ar), 7.62-7.42 (m, 2H, Ar), 7.26-7.23 (m, 3H, Ar), 6.72 (s, 1H, CHPh), 4.99-4.97 (m, 1H, CHCOOCH$_3$), 4.36-4.34 (m, 2H, COCH$_2$Cl), 4.10 (s, 1H, CH$_a$CH$_b$), 3.75 (dd, 1H, J=3.6/7.6 Hz, CH$_a$CH$_b$), 3.49 (s, 3H, OCH$_3$); MS an/z 454 (M$^+$+4), m/z 452 (M$^+$+2), m/z 450 (M$^+$, 100%); Anal. ($C_{21}H_{17}Cl_3N_2O_3$), C, H, N.

Example 33

(1S,3S) Methyl 1-(3,4-dichlorophenyl)-2-(2-chloroacetyl)-2,3,4,9-tetrahydro-1H-β-carboline-3-carboxylate (2o)

White powder; 84%; m.p: 283-284° C.; $R_f$=0.45 ($CH_2Cl_2$); IR (cm$^{-1}$): 3281 (—NH—), 1736 (—CO—), 1662 (—CO—); $^1$H NMR: δ 8.9 (s, 1H, NH), 7.77 (d, 2H, J=8.0 Hz, Ar), 7.61 (d, 2H, J=8.0 Hz, Ar), 7.32-7.17 (m, 3H, Ar), 6.83 (s, 1H, CHPh), 4.98 (d, 1H, J=7.0 Hz, CHCOOCH$_3$), 4.36-4.34 (m, 2H, COCH$_2$Cl), 4.21 (d, 1H, J=3.4/7.6 Hz, CH$_a$CH$_b$), 3.70 (dd, 1H, J=3.4/7.6 Hz, CH$_a$CH$_b$), 3.46 (s, 3H, OCH$_3$);

MS: m/z 454 (M$^+$+4), m/z 452 (M$^+$+2), m/z 450 (M$^+$, 100%); Anal. (C$_{21}$H$_{17}$Cl$_3$N$_2$O$_3$), C, H, N.

Example 34

(1R,3S) Methyl 1-(3,4-dichloro-phenyl)-2 (2-chloro-acetyl)-2,3,4,9-tetrahydro-1H-β-carboline-3-carboxylate (2p)

White powder; 77%; m.p: 162-165° C.; R$_f$=0.24 (CH$_2$Cl$_2$); IR (cm$^{-1}$): 3275 (—NH—), 1738, 1663 (—CO—); $^1$H NMR: δ 7.9 (s, 1H, NH), 7.75 (d, 2H, J=7.6 Hz, Ar), 7.22-7.12 (m, 5H, Ar), 6.03 (s, 1H, CHPh), 4.16 (d, 1H, J=7.0 Hz, CHCOOCH$_3$), 4.13-4.06 (m, 2H, COCH$_2$Cl), 3.61-3.58 (m, 2H, CH$_2$), 3.47 (s, 3H, OCH$_3$); MS: m/z 454 (M$^+$+4), m/z 452 (M$^+$+2), m/z 450 (M$^+$, 100%); Anal. (C$_{21}$H$_{17}$Cl$_3$N$_2$O$_3$), C, H, N.

Example 35

(1R,3R) Methyl 1-(2,6-dichlorophenyl)-2-(2-chloro-acetyl)-2,3,4,9-tetrahydro 1H-β-carboline-3-carboxylate (2q)

Brown powder; 76%; m.p: 147-150° C.; R$_f$=0.44 (100% CH$_2$Cl$_2$); IR (cm$^{-1}$): 3304 (—NH—), 1739, 1666 (—CO—); $^1$H-NMR: δ 8.98 (s, 1H, NH), 7.75-7.15 (m, 7H, Ar), 6.90 (s, 1H, CHPh), 4.99 (s 1H, CHCOOCH$_3$), 4.25-4.22 (m, 2H, COCH$_2$Cl), 3.67 (s, 3H, OCH$_3$), 3.37-3.16 (m, 2H, CH$_2$); MS: m/z 454 (M$^+$+4), m/z 452 (M$^+$+2), m/z 450 (M$^+$), m/z 375 (100%); Anal. (C$_{21}$H$_{17}$Cl$_3$N$_2$O$_3$), C, H, N.

Example 36

(1S,3S) Methyl 1-(2,6-dichlorophenyl)-2-(2-chloro-acetyl)-2,3,4,9-tetrahydro-1H-β-carboline-3-carboxyl (2r)

Brown powder; 78%; m.p: 153-156° C.; R$_f$=0.42 (100% CH$_2$Cl$_2$); IR (cm$^{-1}$): 3309 (—NH—), 1737, 1666 (—CO—); $^1$H-NMR: δ 8.98 (s, 1H, NH), 7.30-7.15 (m, 7H, Ar), 6.90 (s, 1H, CHPh), 4.99 (s, 1H, CHCOOCH$_3$), 4.25-4.21 (m, 2H, COCH$_2$Cl), 3.68 (s, 3H, OCH$_3$), 3.22-3.17 (m, 2H, CH$_2$); MS: m/z 454 (M$^+$+4), m/z 452 (M$^+$+2), m/z 450 (M$^+$), m/z 375 (100%); Anal. (C$_{21}$H$_{17}$Cl$_3$N$_2$O$_3$), C, H, N.

Cell Cultures

All human tumor cell lines were obtained from ATCC and grown under standard cell culture conditions at 37° C. in a humidified atmosphere with 5% CO$_2$. Cells were grown in RPMI 1640 supplemented with 5% fetal bovine serum 2 mM glutamine, 100 units/ml penicillin, 100 units/ml streptomycin, and 0.25 µg/ml amphotericin. Cells were harvested at 70 to 90% confluence with trypsin/EDTA and used immediately Cell count and viability was determined by Trypan blue staining followed by hemocytometry. Only cultures displaying >95% cell viability were used for experiments. HMEC were grown according to the specifications from the supplier (Lonzo).

Growth Assays

Tissue culture microtiter 96-well plates were seeded with cells at a density of 5,000 cells/well. The plates were incubated for 18-24 hours prior to any treatment. All test compounds were solubilized in 100% DMSO and diluted with media to obtain a final DMSO concentration of 0.1%. Cell viability was measured 72 hours after treatment by the Cell Titer Glo Assay (Promega), which is a luminescent assay that is an indicator of live cells as a function of metabolic activity and ATP content. The assay was performed according to manufacturer's specifications. Luminescence was measured by a Perkin Elmer Victor® multi-label plate reader.[6]

cGMP Assay

Cells were seeded at a density of 1×10$^6$ cells per 10 cm tissue culture dish, incubated for 48 hours, and treated with the specified compound or vehicle control. After 30 minutes of treatment, cells were lysed and assayed for cGMP content using the cGMP Direct Biotrak EIA kit (GE Biosciences). The assay was performed according to the manufacturer's specifications. Optical density was measured at 630 nm using a Synergy4 (BioTek) plate reader.

Experimental Design and Data Analysis

The potency of compounds to inhibit tumor cell growth was expressed by an IC$_{50}$ value (50% inhibitory concentration). The IC$_{50}$ value was determined by testing a range of 8 concentrations with at least four replicates per concentration. Dose response curves were analyzed using Prism™ 4 software (GraphPad) to calculate IC$_{50}$ values using a four parameter logistic equation.

Formulations

Compounds of the present disclosure can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice. The compounds can also be administered in conjunction with other prevention or therapeutic agents if desired.

The pharmaceutically acceptable carriers described herein, for example, vehicles, adjuvants, excipients, or diluents, are well-known to those who are skilled in the art. Typically, the pharmaceutically acceptable carrier is chemically inert to the active compounds and has no detrimental side effects or toxicity under the conditions of use. The pharmaceutically acceptable carriers can include polymers and polymer matrices.

The compounds of this disclosure can be administered by any conventional method available for use in conjunction with pharmaceuticals, either as individual therapeutic agents or in a combination of therapeutic agents.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 1000 milligrams (mg) per kilogram (kg) of body weight, with the preferred dose being 0.1 to about 30 mg/kg.

Dosage forms (compositions suitable for administration) typically contain from about 1 mg to about 500 mg of active ingredient per unit. In these pharmaceutical compositions, the active ingredient will ordinarily be present in an amount of about 0.5-95% weight based on the total weight of the composition.

The active ingredient can be administered orally in solid dosage forms, such as capsules, tablets, and powders, or in liquid dosage forms, such as elixirs, syrups and suspensions. It can also be administered parenterally, in sterile liquid dosage forms. The active ingredient can also be administered intranasally (nose drops) or by inhalation of a drug powder mist. Other dosage forms are potentially possible such as administration transdermally, via patch mechanism or ointment.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, propylene glycol, glycerin, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of the following: lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acadia, emulsions, and gels containing, in addition to the active ingredient, such carriers as are known in the art.

The compounds of the present disclosure, alone or in combination with other suitable components, can be made into aerosol formulations to be administered via inhalation. These aerosol formulations can be placed into pressurized acceptable propellants, such as dichlorodifluoromethane, propane, and nitrogen. They also may be formulated as pharmaceuticals for non-pressured preparations, such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol such as poly(ethyleneglycol) 400, glycerol ketals, such as 2,2-dimethyl-1,3-dioxolane-4-methanol, ethers, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyldialkylammonium halides, and alkylpyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene polypropylene copolymers, (d) amphoteric detergents such as, for example, alkyl β-aminopropionates, and 2-alkylimidazoline quaternary ammonium salts, and (e) mixtures thereof.

The parenteral formulations typically contain from about 0.5% to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

Pharmaceutically acceptable excipients are also well-known to those who are skilled in the art. The choice of excipient will be determined in part by the particular compound, as well as by the particular method used to administer the composition. Accordingly, there is a wide variety of suitable formulations of the pharmaceutical composition of the present disclosure. The following methods and excipients are merely exemplary and are in no way limiting. The pharmaceutically acceptable excipients preferably do not interfere with the action of the active ingredients and do not cause adverse side-effects. Suitable carriers and excipients include solvents such as water, alcohol, and propylene glycol, solid absorbants and diluents, surface active agents, suspending agent, tableting binders, lubricants, flavors, and coloring agents.

The formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, Eds., 238-250 (1982) and *ASHP Handbook on Injectable Drugs*, Toissel, 4th ed., 622-630 (1986).

Formulations suitable for topical administration include lozenges comprising the active ingredient in a flavor, usually sucrose and acacia or tragacanth; pastilles comprising the active ingredient in an inert base, such as gelatin and glycerin, or sucrose and acacia; and mouthwashes comprising the active ingredient in a suitable liquid carrier; as well as creams, emulsions, and gels containing, in addition to the active ingredient, such carriers as are known in the art.

Additionally, formulations suitable for rectal administration may be presented as suppositories by mixing with a variety of bases such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

Suitable pharmaceutical carriers are described in Remington's Pharmaceutical Sciences, Mack Publishing Company, a standard reference text in this field.

The dose administered to an animal, particularly a human, in the context of the present disclosure should be sufficient to affect a therapeutic response in the animal over a reasonable time frame. One skilled in the art will recognize that dosage will depend upon a variety of factors including a condition of the animal, the body weight of the animal, as well as the severity and stage of the condition being treated.

A suitable dose is that which will result in a concentration of the active agent in a patient which is known to affect the desired response. The preferred dosage is the amount which results in maximum inhibition of the condition being treated, without unmanageable side effects.

The size of the dose also will be determined by the route, timing and frequency of administration as well as the existence, nature, and extend of any adverse side effects that might accompany the administration of the compound and the desired physiological effect.

Useful pharmaceutical dosage forms for administration of the compounds according to the present disclosure can be illustrated as follows:

Hard Shell Capsules

A large number of unit capsules are prepared by filling standard two-piece hard gelatin capsules each with 100 mg of powdered active ingredient, 150 mg of lactose, 50 mg of cellulose and 6 mg of magnesium stearate.

Soft Gelatin Capsules

A mixture of active ingredient in digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets

A large number of tablets are prepared by conventional procedures so that the dosage unit was 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules

These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Moreover, the compounds of the present disclosure can be administered in the form of nose drops, or metered dose and a nasal or buccal inhaler. The drug is delivered from a nasal solution as a fine mist or from a powder as an aerosol.

All publications, patents and patent applications cited in this specification are herein incorporated by reference, and for any and all purpose, as if each individual publication, patent or patent application were specifically and individually indicated to be incorporated by reference. In the case of inconsistencies, the present disclosure will prevail.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The embodiments described hereinabove are further intended to explain best modes known of practicing it and to enable others skilled in the art to utilize the disclosure in such, or other, embodiments and with the various modifications required by the particular applications or uses. Accordingly, the description is not intended to limit it to the form disclosed herein. Also, it is intended that the appended claims be construed to include alternative embodiments.

REFERENCES (1) Lugnier C. Cyclic Nucleotide Phosphodiesterase (PDE) Superfamily: A New Target for the Development of Specific Therapeutic Agents. *Pharmacol. Ther.*, 2006, 109, 366-98.

(2) Bender A. T.; Beavo J. A. Cyclic Nucleotide Phosphodiesterases: Molecular Regulation to Clinical Use. *Pharmacol. Rev.*, 2006, 58, 488-520.

(3) Frajese G. V.; Pozzi F. New Achievement and Novel Therapeutic Applications of PDE5 Inhibitors in Older Males. *J Endocrinol Invest*, 2005, 28, 45-50.

(4) Piazza G. A.; Thompson W. J.; Pamukcu R.; Alila H. W.; Whitehead C. M.; Liu L.; Fetter J. R.; Gresh W. E., Jr.; Klein-Szanto A. J.; Farnell D. R.; Eto I.; Grubbs C. J. Exisulind, a Novel Proapoptotic Drug, Inhibits Rat Urinary Bladder Tumorigenesis. *Cancer Res.*, 2001, 61, 3961-8.

(5) Zhu B.; Vemavarapu L.; Thompson W. J.; Strada S. J. Suppression of Cyclic GMP-Specific Phosphodiesterase 5 Promotes Apoptosis and Inhibits Growth in Ht29 Cells. *J. Cell. Biochem.*, 2005, 94, 336-50.

(6) Thompson W. J.; Piazza G. A.; Li H.; Liu L.; Fetter J.; Zhu B.; Sperl G.; Ahnen D.; Pamukcu R. Exisulind Induction of Apoptosis Involves Guanosine 3',5'-Cyclic Monophosphate Phosphodiesterase Inhibition, Protein Kinase G Activation, and Attenuated Beta-Catenin. *Cancer Res.*, 2000, 60, 3338-42.

(7) Liu L.; Li H.; Underwood T.; Lloyd M.; David M.; Sperl G.; Pamukcu R.; Thompson W. J. Cyclic GMP-Dependent Protein Kinase Activation and Induction by Exisulind and Cp461 in Colon Tumor Cells. *J Pharmacol Exp. Ther.*, 2001, 299, 583-92.

(8) Donodoni A.; Perrone D. Synthesis of 1,1-Dimethylethyl (S)-4-Formyl-2,2-Dimethyl-3-Oxazolidinedcarboxylate by Oxidation of the Alcohol. *Org. Synth.*, 2004, 10, 320.

(9) Ungemach F.; Sorens D.; Weber R.; Dipierro M.; Campos O.; Mokry P.; Cook J M. General Method for the Assignment of Stereochemistry of 1,3-Disubstituted-1,2,3,4-Tetrahydro-β-Carbolines by Carbon-13 Spectroscopy, J. Am. Chem. Soc. 1980, 102, 6976.

(10) Sandrin J.; Soerens J.; Cook J M. $^{13}$C-NMR of 1,3-Disubstituted 1,2,3,4-Tetrahydro-β-Carbolines, Heterocycles 1976, 4, 1249.

(11) Sunder-Plassmann N.; Sarli V.; Gartner M.; Utz M.; Seiler J.; Huemmer S.; Mayer T. U.; Surrey T.; Giannis A. Synthesis and Biological Evaluation of New Tetrahydro-Beta-Carbolines as Inhibitors of the Mitotic Kinesin Eg5. *Bioorg. Med. Chem.*, 2005, 13, 6094-111.

(12) Daugan A.; Grondin P.; Ruault C.; Le Monnier de Gouville A. C.; Coste H.; Kirilovsky J.; Hyafil F.; Labaudiniere R. The Discovery of Tadalafil: A Novel and Highly Selective PDE5 Inhibitor. 1: 5,6,11,11a-Tetrahydro-1h-Imidazo[1',5': 1,6]Pyrido[3,4-B]Indole-1,3(2h)-Dione Analogues. J. Med. Chem., 2003, 46, 4525-32.

What is claimed is:

1. A compound represented by the formulae (1) or (2):

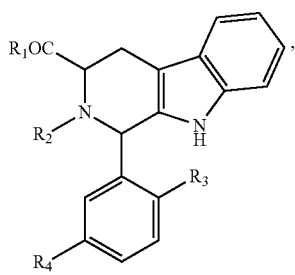

(1)

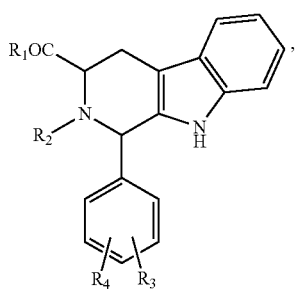

(2)

wherein in formula (1) $R_1$ is a hydroxy function or an alkoxy group containing 1-4 carbon atoms; $R_2$ is a acyl halo group containing 2-5 carbon atoms; $R_3$ is a halo group or an alkoxy group containing 1-4 carbon atoms and $R_4$ is H when $R_3$ is halo and is an alkoxy group containing 1-4 carbon atoms when $R_3$ is an alkoxy group containing 1-4 carbon atoms; wherein in formula (2), $R_1$ is a hydroxy or an alkoxy group containing 1-4 carbon atoms; $R_2$ is an acyl halo group containing 2 carbon atoms; $R_3$ is a halo group and $R_4$ is halo; pharmaceutically acceptable salt thereof or solvates thereof.

2. A compound according to claim 1 being represented by formula 1, pharmaceutically acceptable salt thereof or solvates thereof.

3. A compound according to claim 1 being represented by formula 2, pharmaceutically acceptable salt thereof or solvates thereof.

4. A compound according to claim 1 wherein $R_3$ is chloro or bromo.

5. A compound according to claim 1 wherein $R_4$ is selected from the group consisting of hydrogen, methoxy and chloro.

6. A compound according to claim 1 wherein $R_2$ is ethanoyl chloride.

7. A compound selected from the group consisting of:
methyl-1-(2-bromophenyl)-2-(2-chloroacetyl)-2,3,4,9-tetrahydro-1H-β-carboline-3-carboxylate;
methyl-1-(2,5-dimethoxyphenyl)-2-(2-chloroacetyl)-2,3,4,9-tetrahydro-1H-β-carboline-3-carboxylate;
methyl 1-(2,4-dichlorophenyl)-2-(2-chloroacetyl)-2,3,4,9-tetrahydro-1H-β-carboline-3-carboxylate;
methyl 1-(3,4dichlorophenyl)-2-(2-chloroacetyl)-2,3,4,9-tetrahydro-1H-β-carboline-3-carboxylate; and
methyl 1-(2,6-dichlorophenyl)-2-(2-chloroacetyl)-2,3,4, 9-tetrahydro 1H-β-carboline-3-carboxylate;
pharmaceutically acceptable salt thereof or solvates thereof.

8. A compound selected from the group consisting of:
methyl (1R,3R)-1-(2-bromophenyl)-2-(2-chloroacetyl)-2, 3,4,9-tetrahydro-1H-β-carboline-3-carboxylate;
methyl (1S,3R)-1-(2-bromophenyl)-2-(2-chloroacetyl)-2, 3,4,9-tetrahydro-1H-β-carboline-3-carboxylate;
methyl (1S,3S)-1-(2-bromophenyl)-2-(2-chloroacetyl)-2, 3,4,9-tetrahydro-1H-β-carboline-3-carboxylate;
methyl (1R,3S)-1-(2-bromophenyl)-2-(2-chloroacetyl)-2, 3,4,9-tetrahydro-1H-β-carboline-3-carboxylate;
methyl (1R,3R)-1-(2,5-dimethoxyphenyl)-2-(2-chloroacetyl)-2,3,4,9-tetrahydro-1H-β-carboline-3-carboxylate;
methyl (1S,3R)-1-(2,5-dimethoxyphenyl)-2-(2-chloroacetyl)-2,3,4,9-tetrahydro-1H-β-carboline-3-carboxylate;
methyl (1S,3S)-1-(2,5-dimethoxyphenyl)-2-(2-chloroacetyl)-2,3,4,9-tetrahydro-1H-β-carboline-3-carboxylate;
methyl (1R,3S)-1-(2,5-dimethoxyphenyl)-2-(2-chloroacetyl)-2,3,4,9-tetrahydro-1H-β-carboline-3-carboxylate;
(1S,3R) methyl 1-(2,4-dichlorophenyl)-2-(2-chloroacetyl)-2,3,4,9-tetrahydro-1H-β-carboline-3-carboxylate;
(1S,3S) methyl 1-(2,4dichlorophenyl)-2-(2-chloroacetyl)-2,3,4,9-tetrahydro-1H-β-carboline-3-carboxylate;
(1R,3S) methyl 1-(2,4dichlorophenyl)-2-(2-chloroacetyl)-2,3,4,9-tetrahydro-1H-β-carboline-3-carboxylate;
(1R,3R) methyl 1-(3,4dichlorophenyl)-2-(2-chloroacetyl)-2,3,4,9-tetrahydro-1H-β-carboline-3-carboxylate;
(1S,3R) methyl 1-(3,4dichlorophenyl)-2-(2-chloroacetyl)-2,3,4,9-tetrahydro-1H-β-carboline-3-carboxylate;
(1S,3S) methyl 1-(3,4-dichlorophenyl)-2-(2chloroacetyl)-2,3,4,9-tetrahydro-1H-β-carboline-3-carboxylate;
(1R,3S) methyl 1-(3,4-dichloro-phenyl)-2(2-chloroacetyl)-2,3,4,9-tetrahydro-1H-β-carboline-3-carboxylate;
(1R,3R) methyl 1-(2,6-dichlorophenyl)-2-(2-chloroacetyl)-2,3,4,9-tetrahydro 1H-β-carboline-3-carboxylate;
(1S,3S) methyl 1-(2,6-dichlorophenyl)-2-(2-chloroacetyl)-2,3,4,9-tetrahydro-1H-β-carboline-3-carboxyl;
pharmaceutically acceptable salt thereof or solvates thereof.

9. A pharmaceutical composition containing a compound according to claim 1; pharmaceutically acceptable salt thereof or solvate thereof.

10. A pharmaceutical composition containing a compound according to claim 2; pharmaceutically acceptable salt thereof or solvate thereof.

11. A pharmaceutical composition containing a compound according to claim 3; pharmaceutically acceptable salt thereof or solvate thereof.

12. A pharmaceutical composition containing a compound according to claim 4; pharmaceutically acceptable salt thereof or solvate thereof.

13. A pharmaceutical composition containing a compound according to claim 5; pharmaceutically acceptable salt thereof or solvate thereof.

14. A pharmaceutical composition containing a compound according to claim 6; pharmaceutically acceptable salt thereof or solvate thereof.

* * * * *